(12) United States Patent
Parfitt et al.

(10) Patent No.: US 8,894,925 B2
(45) Date of Patent: Nov. 25, 2014

(54) TREATING FLAMMABLE MATERIALS

(75) Inventors: Alexander Roy Parfitt, Wiltshire (GB); Ivor Andrew Williams, Cheshire (GB); David William Gough, Bristol (GB); Jason Karl Rew, Bristol (GB); Alexander Dalling, Lanarkshire (GB); Davia Jean-Louis Gutierrez, Glasgow (GB)

(73) Assignee: BAE SYSTEMS plc, London (GB)

( * ) Notice: Subject to any disclaimer, the term of this patent is extended or adjusted under 35 U.S.C. 154(b) by 936 days.

(21) Appl. No.: 13/062,490

(22) PCT Filed: Sep. 2, 2009

(86) PCT No.: PCT/GB2009/051102
§ 371 (c)(1),
(2), (4) Date: Jun. 8, 2011

(87) PCT Pub. No.: WO2010/026416
PCT Pub. Date: Mar. 11, 2010

(65) Prior Publication Data
US 2011/0236255 A1 Sep. 29, 2011

(30) Foreign Application Priority Data

Sep. 4, 2008 (EP) .................................... 08275049
Sep. 4, 2008 (GB) .................................... 0816117.6

(51) Int. Cl.
| A61L 2/00 | (2006.01) |
| F02M 27/06 | (2006.01) |
| A61L 2/10 | (2006.01) |
| A61L 9/20 | (2006.01) |
| C10G 32/02 | (2006.01) |

(52) U.S. Cl.
CPC *F02M 27/06* (2013.01); *A61L 2/10* (2013.01); *A61L 9/20* (2013.01); *C10G 32/02* (2013.01)
USPC ................................. 422/24; 422/22; 422/23

(58) Field of Classification Search
CPC ......................................................... A61L 2/10
USPC .......................................... 422/4, 22, 23, 24
See application file for complete search history.

(56) References Cited

U.S. PATENT DOCUMENTS

| 3,246,144 A | 4/1966 | Beall et al. |
| 3,674,421 A | 7/1972 | Decupper |

(Continued)

FOREIGN PATENT DOCUMENTS

| CA | 2 365 148 A1 | 6/2003 |
| GB | 2 412 319 A | 9/2005 |

(Continued)

OTHER PUBLICATIONS

International Search Report (PCT/ISA/210) dated Nov. 5, 2009.

(Continued)

*Primary Examiner* — Regina M Yoo
(74) *Attorney, Agent, or Firm* — Finch & Maloney PLLC

(57) ABSTRACT

A method and device are provided for treating flammable materials, fuels for example, by irradiation of the materials with ultra-violet radiation. In one embodiment, the apparatus suited for connection to a fuel line includes a body with centrally-formed duct and UV light sources mounted outside of the duct at upper and lower sides. It is to be appreciated that the invention has utility for many different fuel system applications, for example in aircraft, boats and in other motive vehicles. Further, the device can be conveniently mounted, if desired, on different fuel platforms including on bowsers.

19 Claims, 21 Drawing Sheets

(56) References Cited

U.S. PATENT DOCUMENTS

| | | |
|---|---|---|
| 4,337,119 A | 6/1982 | Donahue |
| 5,505,904 A | 4/1996 | Haidinger et al. |
| 5,622,622 A | 4/1997 | Johnson |
| 5,997,812 A | 12/1999 | Burnham et al. |
| 2002/0132143 A1 | 9/2002 | Itou et al. |
| 2003/0131734 A1 | 7/2003 | Engel et al. |
| 2008/0110802 A1 | 5/2008 | Gondal et al. |

FOREIGN PATENT DOCUMENTS

| | | |
|---|---|---|
| RU | 2 249 610 C1 | 4/2005 |
| WO | WO 96/22944 A1 | 8/1996 |

OTHER PUBLICATIONS

Written Opinion (PCT/ISA/237) dated Nov. 5, 2009.
European Search Report (EPO Form 1507N) dated Feb. 25, 2009.
Great Britain Search Report dated Oct. 10, 2008.

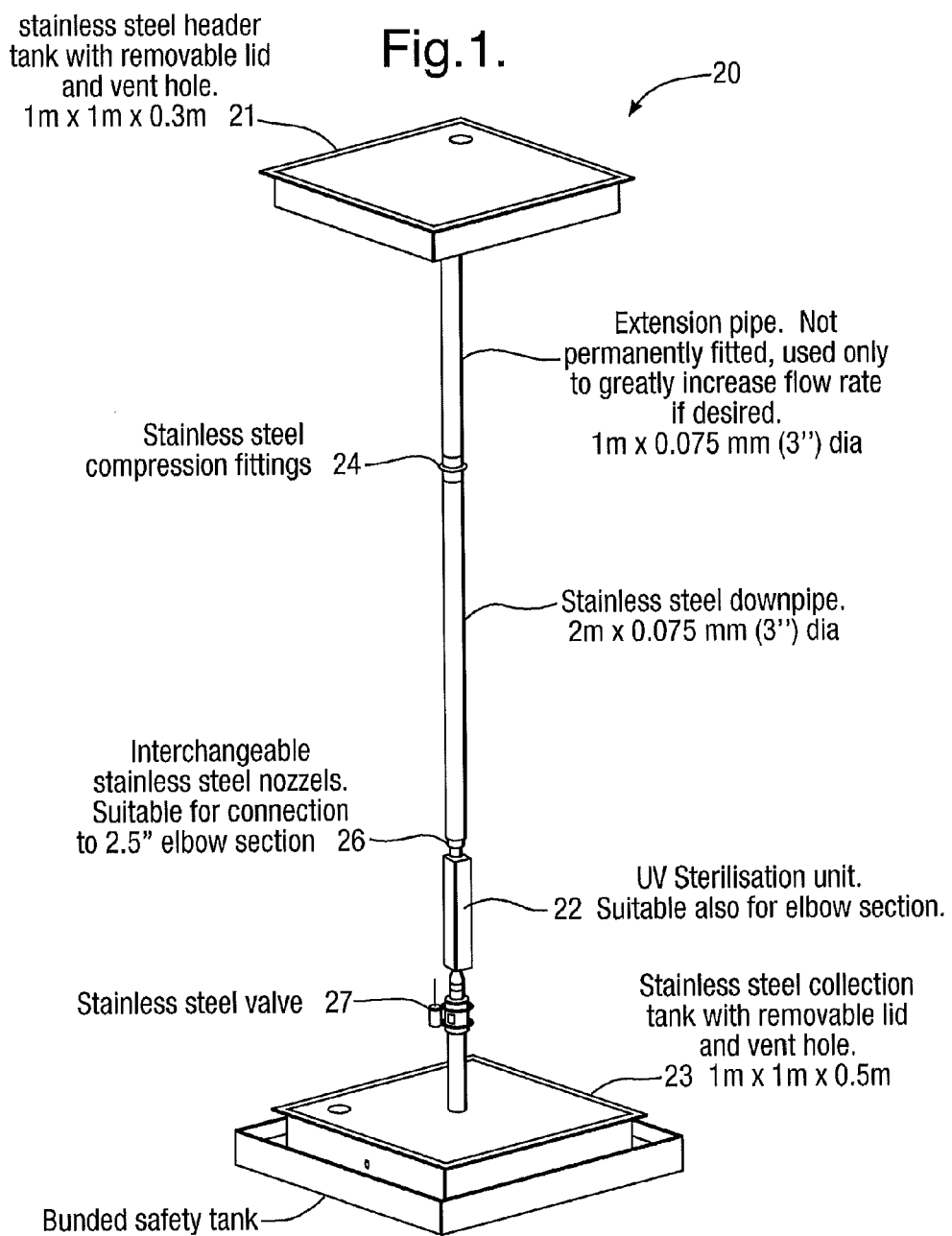

Lowest Concentration

Medium - Low

Medium Concentration

Medium - High

Highest Concentration

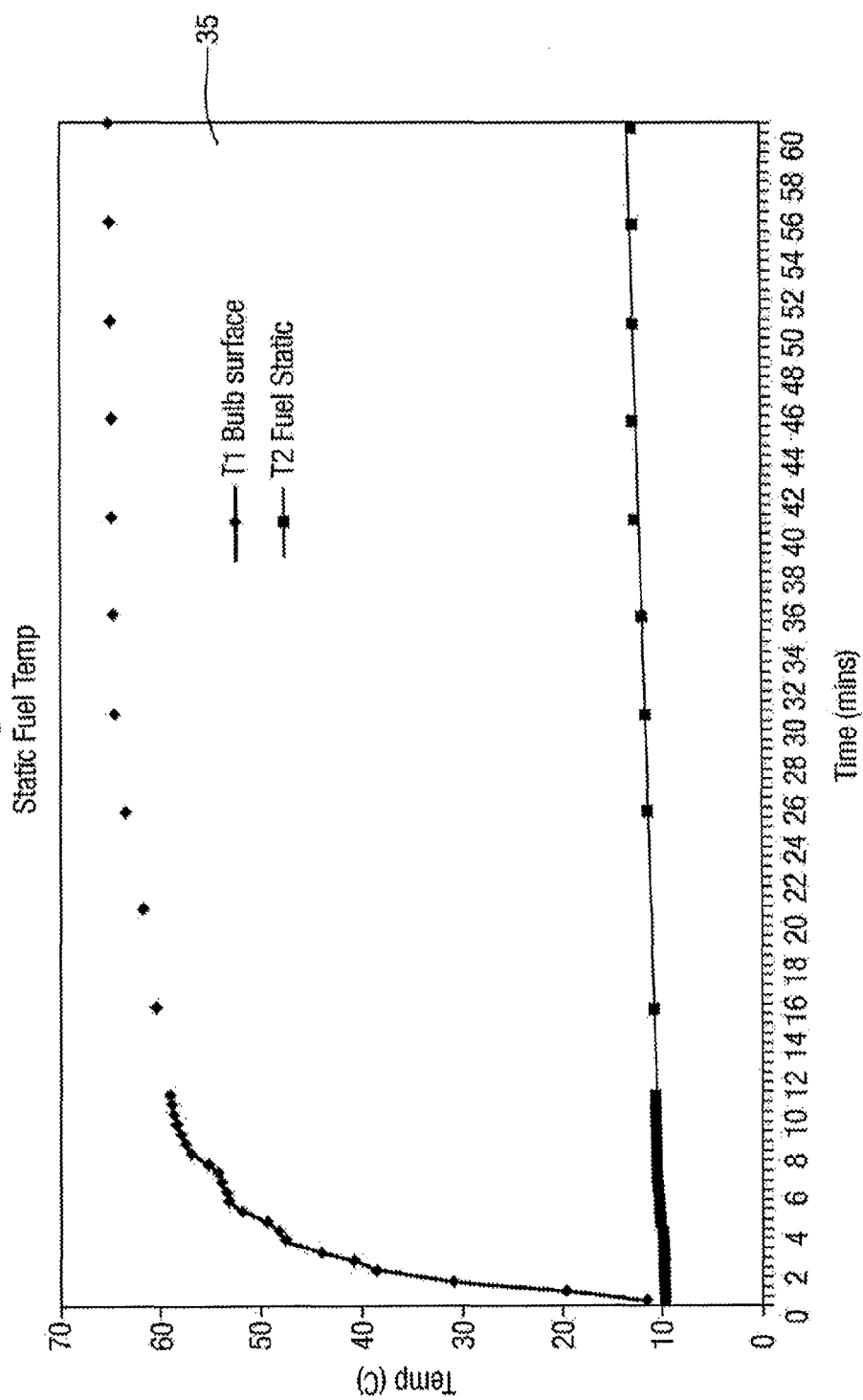

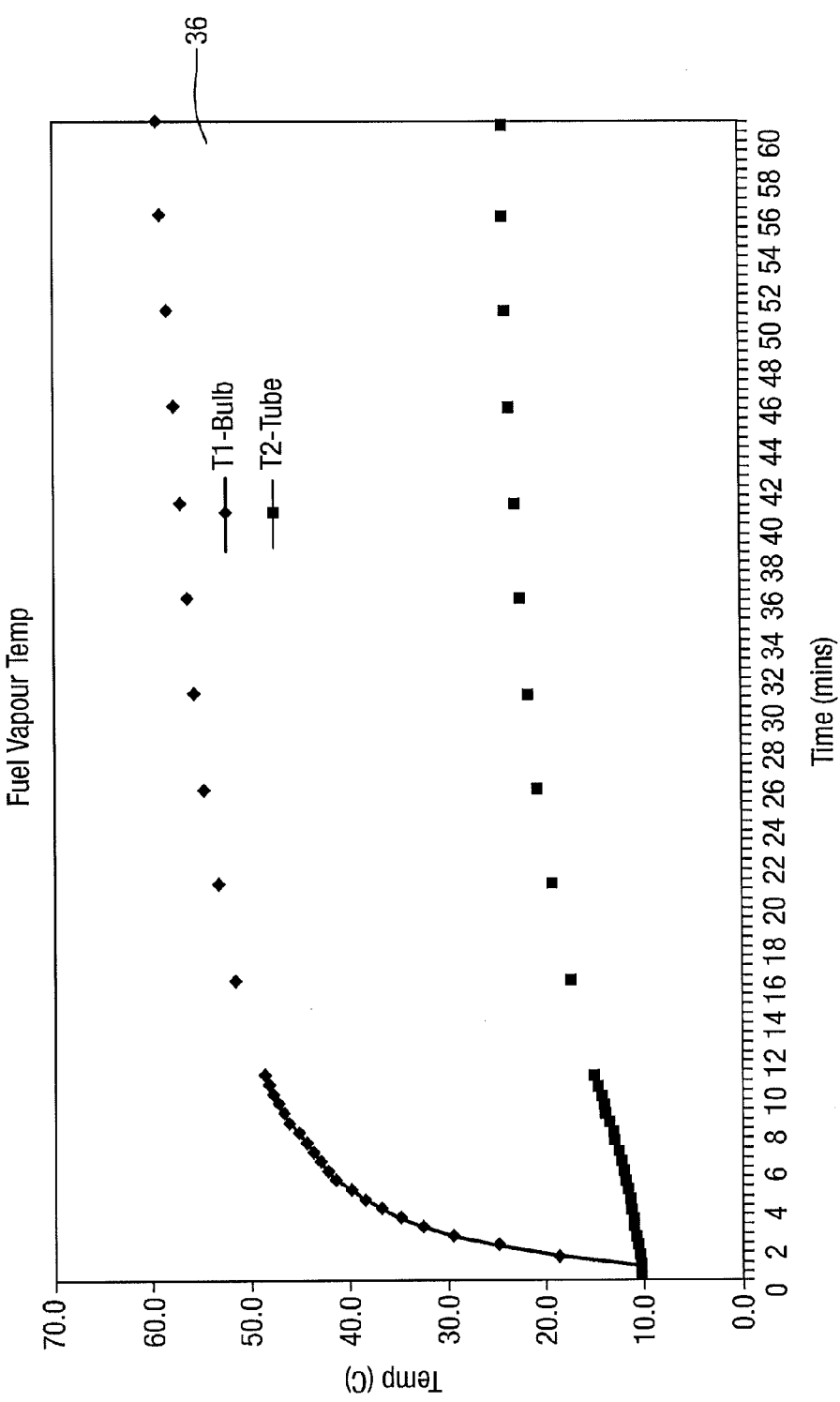

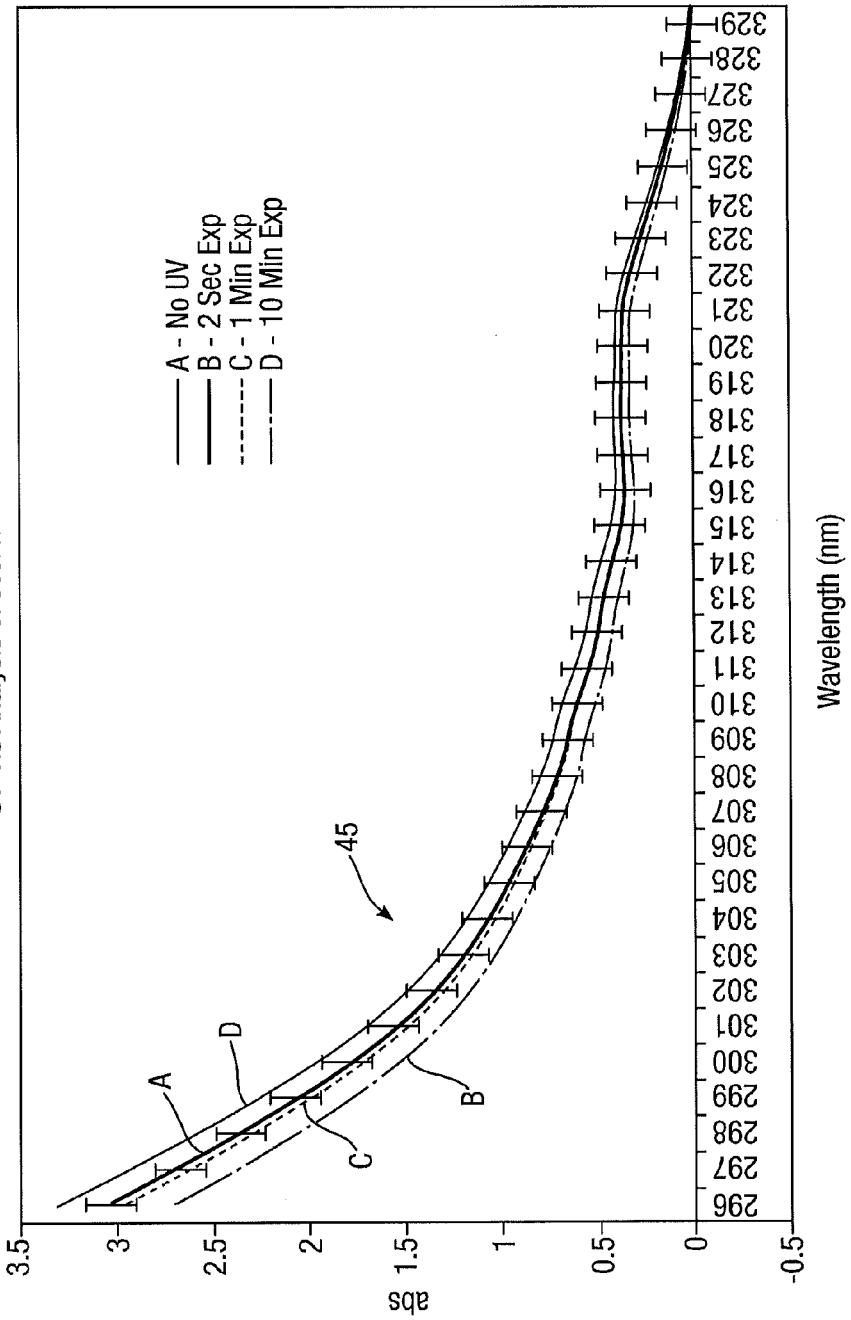

Black section indicates the position of the refuel panel on the underside of the leading edge.

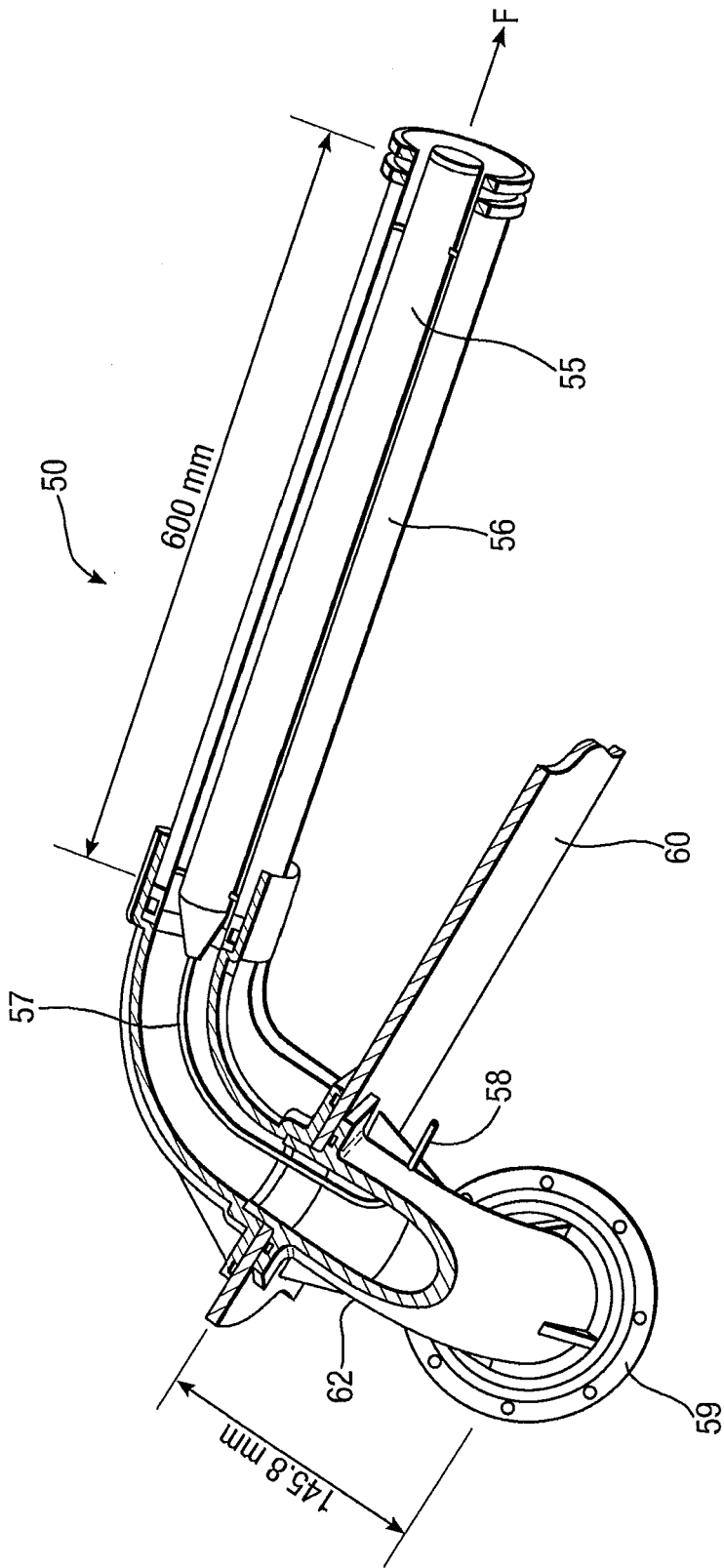

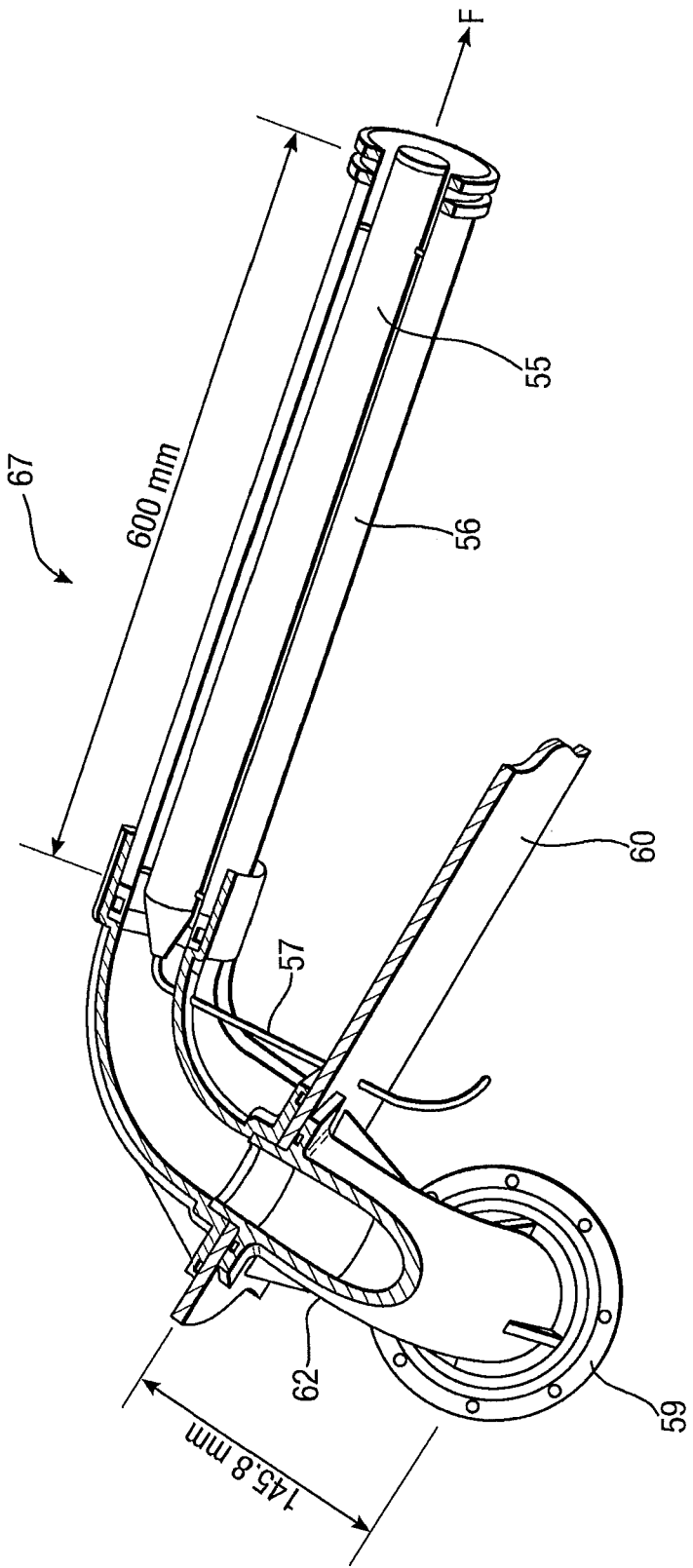

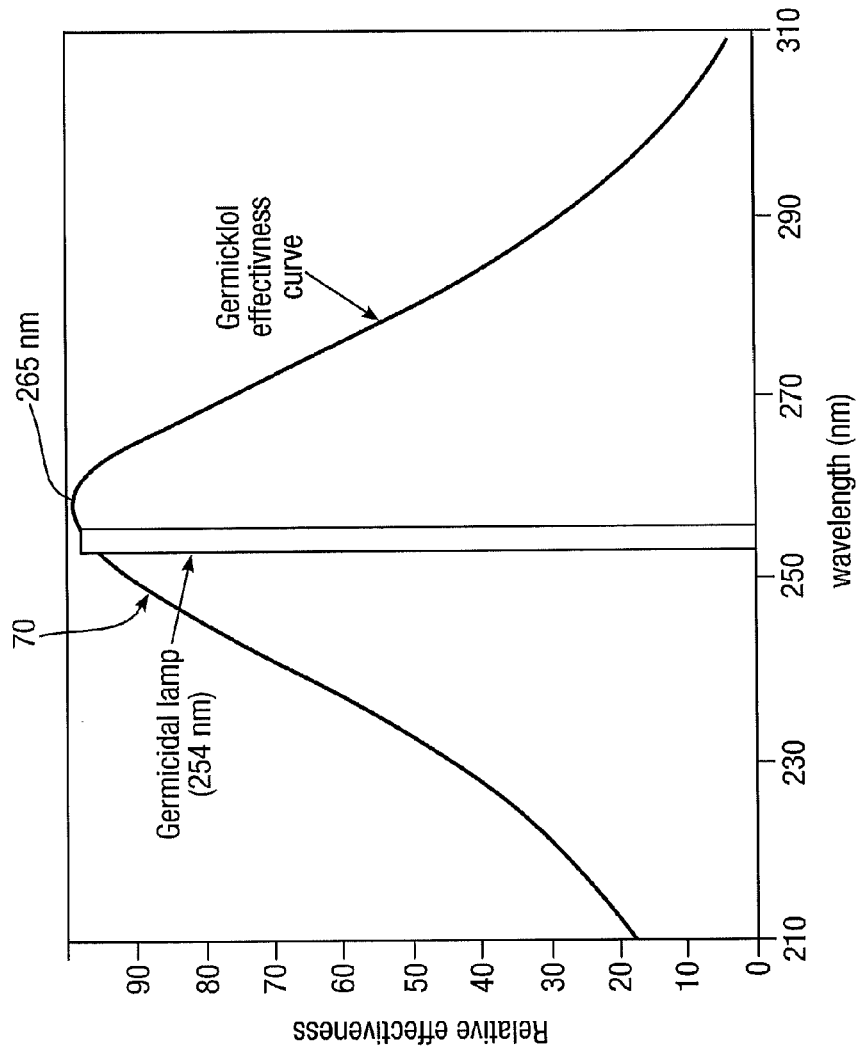

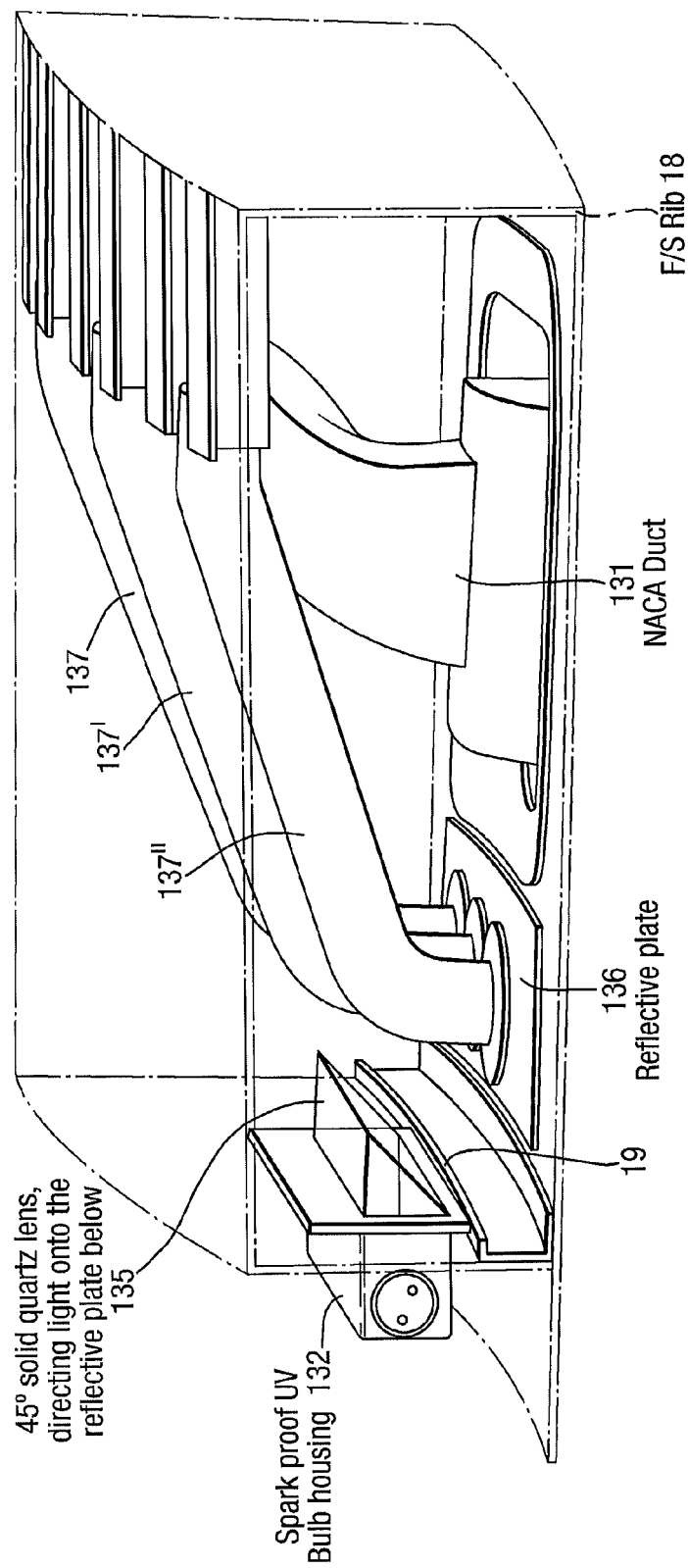

TREATING FLAMMABLE MATERIALS

FIELD OF THE INVENTION

This invention relates to a method and apparatus for treating flammable materials and particularly, but not exclusively, to a method and apparatus for treating fuels.

BACKGROUND OF THE INVENTION

Fuel, aviation fuel for example, is known to become contaminated with microorganisms which are naturally present in air. The microorganisms include bacteria, moulds, protozoa, viruses and yeasts. The problem of fuel contamination in fuel systems is inevitable because fuel systems do not operate in sterile environments and the fuel is routinely exposed to air during its life-cycle. Once such microorganisms are in the fuel, their growth invariably occurs especially in hot and humid environments at any fuel-water interface, typically resulting in large colonies forming on the side walls of the aircraft fuel tanks. These colonies (also referred to as biofilms) if not treated, may block filters and more seriously corrode the storage vessel/system structure via the release of acidic by-products.

Ultra-violet (UV) irradiation is extensively used in water purification systems as a germicidal treatment method. It is used in industrial-scale water supply applications as well as in smaller-scale domestic applications (for example, in swimming pools, ponds and aquaria). It is also used to sterilise work surfaces in for example industrial food processing/packaging applications and air ventilation systems. Ultra-violet irradiation has been shown to inactivate a diverse range of microorganisms and achieves this by means of lethal disruption to the nucleic acid bases (DNA and RNA), thereby rendering the microorganisms unusable.

GB2412319 describes an apparatus for disinfecting air flowing along a duct in an air conditioning or ventilating system. The disinfection is achieved using ultra-violet irradiation.

RU2249610 (see the English-language abstract) concerns a method of controlling microbiological damage. There is no enabling disclosure in RU2249610 of treating fuels predominantly with ultra-violet radiation, and indeed RU2249610 appears to teach against the particular suitability of ultra-violet radiation for the treatment of aviation fuels.

U.S. Pat. No. 3,246,144 describes the inhibition of microorganism growth in petroleum fuel using ultra-violet irradiation, but it is noted that the present inventors are unaware of any successful implementation of the apparatus disclosed therein.

Note also that the significant problem of microbial contamination of stored hydrocarbon fuels has been discussed in the published literature, see for example C Gaylarde et al. Revista de Microbiologia (1999) 30:01-10 ISSN 0001-3714.

SUMMARY OF THE INVENTION

Accordingly, the present invention aims to overcome or at least substantially reduce some of the above mentioned drawbacks.

In broad terms, the present invention resides in the realisation of using ultra-violet radiation for the treatment of flammable materials including liquid fuels, and in the methods and apparatus which implement this realisation.

The term "ultra-violet radiation" in the present specification and claims is understood to refer to electromagnetic radiation in the wavelength band of 100-400 nm. Further, we have found that ultra-violet radiation in the wavelength band of 100-290 nm is particularly effective for the treatment of fuels.

Against this background, in one aspect, this invention provides a method of treating a flammable material which comprises irradiating the flammable material with predominantly ultra-violet radiation causing a significant proportion of microorganisms in the material to be sterilised.

Preferably, the method includes a step of irradiating the flammable material with ultra-violet radiation in the wavelength range of between about 100 nm and 290 nm. Optionally, the method includes a step of irradiating the flammable material with ultra-violet radiation in the wavelength range of between about 240 nm and 280 nm. Optionally, the ultra-violet radiation has a wavelength predominantly at 254 nm.

The flammable material may comprise flammable liquids and flammable solids. Preferably, the flammable material is a fuel, for example a liquid fuel. Optionally, the fuel may be diesel fuel. The diesel fuel may for example be marine diesel fuel. Optionally, the fuel may be petrol fuel. Optionally, the fuel may be kerosene fuel. Optionally, the fuel may be an aviation fuel. Conveniently, the fuel may be a jet fuel, for example JET A1 fuel.

Conveniently, the fuel may be a biofuel.

Optionally, the flammable material may be fuel vapour. Conveniently, the fuel vapour may be treated in a fluid. For example, the fluid may be air.

In another aspect, this invention provides an apparatus for treating a flammable material, the apparatus comprising means for irradiating the flammable material with predominantly ultra-violet radiation causing a significant proportion of microorganisms in the material to be sterilised.

In one embodiment, the apparatus for connection to a fuel line for treating fuel in the fuel line may comprise: a sleeve made of a material substantially transparent to ultra-violet radiation; an ultra-violet light source for irradiating fuel which flows along the fuel line with ultra-violet radiation; said source being arranged to extend axially along the interior of said sleeve; and said source and sleeve being mounted at predetermined locations within the fuel line. The term "material substantially transparent" is used here to mean that the material transmits at least 90% at the mid-value of the ultra-violet wavelength band. The fuel line may be an aircraft fuel line for example.

The ultra-violet light source in the abovementioned embodiment conveniently is an elongate ultra-violet lamp.

In another embodiment, the ultra-violet light source may be a curved ultra-violet light source (lamp) in which the source is arranged to follow a path which includes a U-shaped bend. Optionally, the source comprises a first and a second section for irradiating fuel with ultra-violet radiation, and the sections are spaced to define a gap therebetween. Conveniently, the first and second sections are elongate sections, and the gap is located at the U-shaped bend. It is to be further understood that one or more sections of the source may be removed to provide two or more separate, elongate light sources (lamps), if desired.

Optionally, the sleeve in the abovementioned embodiment is formed of quartz material.

In another embodiment, the apparatus for connection to a fuel line for treating fuel in the fuel line may comprise: means defining a mounting for at least one ultra-violet light source with associated window means; means defining a duct for channelling fuel flow along the fuel line; said at least one ultra-violet light source with associated window means being disposed on one side of the duct outside of the fuel line such that in use of the apparatus the ultra-violet radiation from said at least one source irradiates the fuel via said associated window means as the fuel flows along the duct; and said associated window means is made of material substantially transparent to the ultra-violet radiation. The term "window means" is used here broadly to mean an element capable of transmitting radiation in the ultra-violet wavelength band and includes lenses, fibre-optic elements as well as refractive and diffractive elements generally. The term "material substantially transparent" is used to mean that the window means transmits at least 90% at the mid-value of the ultra-violet wavelength band. The fuel line may be an aircraft fuel line for example.

In another embodiment, the apparatus for connection to a fuel line for treating fuel in the fuel line may comprise: means defining a mounting for a plurality of ultra-violet light sources; means defining a duct for channelling fuel flow along the fuel line; at least one of said ultra-violet light sources with associated window means being disposed on one side of the duct outside of the fuel line and another of said ultra-violet light sources with associated window means being disposed on the opposing side of the duct outside of the fuel line such that in use of the apparatus the ultra-violet radiation from one or more of the sources irradiates the fuel via said associated window means as the fuel flows along the duct; and each said associated window means is made of material substantially transparent to the ultra-violet radiation. As discussed above, the term "window means" is again used broadly to mean an element capable of transmitting radiation in the ultra-violet wavelength band and includes lenses, fibre-optic elements as well as refractive and diffractive elements generally. The term "material substantially transparent" is again used to mean that the window means transmits at least 90% at the mid-value of the ultra-violet wavelength band. Conveniently in this embodiment, the or each of said window means is formed of quartz material. The fuel line may be an aircraft fuel line for example.

In another embodiment, the apparatus is mounted at a predetermined location of a surge tank unit, permitting air which carries the flammable material to be treated as the air is allowed to enter the associated fuel tanks of said unit. Optionally, the air may be treated at a predetermined entry point, for example as applied to aircraft this may be at a common entry point at which outside air is allowed to enter into the aircraft. Optionally, air may be treated at a predetermined point inside the surge tank area as the air is allowed to flow inside said surge tank area. In test aircraft, air is thus treated at the surge tank area (in this particular case, the air is not flowing inside a duct at the point of treatment). Optionally, the apparatus may comprise: means defining a mounting for at least one ultra-violet light source; said at least one ultra-violet light source with associated window means being disposed on one side of the surge tank unit such that in use of the apparatus the ultra-violet radiation from said at least one source irradiates air as the air flows along a duct in the tank unit; and said window means is made of material substantially transparent to the ultra-violet radiation. Optionally, the ultra-violet radiation may be directed at a reflective element in the surge tank unit, permitting air to be treated with the radiation reflected by said reflective element. Conveniently, the light source mounting may be mounted adjacent and outside of the tank unit. The window means advantageously may be a lens formed of quartz material.

The present invention extends to the above described apparatus mounted on a refuelling vehicle. Optionally, the refuelling vehicle may be a bowser. Optionally, the refuelling vehicle may be a hydrant refuelling vehicle. Optionally, the refuelling vehicle may be based on a combination of a bowser and a hydrant vehicle.

The present invention extends to the above described apparatus mounted at a predetermined location inside a fuel storage vessel/tank.

In order to effect the treatment of fuels, in aircraft fuel lines for example, the apparatus conveniently provides ultra-violet radiation in the wavelength range of between about 100 nm and 290 nm. Optionally, the ultra-violet radiation may be in the wavelength range of between about 240 nm and 280 nm. Optionally, the ultra-violet radiation has a wavelength predominantly at 254 nm. Conveniently, a mercury light source (bulb) may be used to provide ultra-violet radiation with wavelength predominantly at 254 nm. Such mercury light sources are commercially available and can be purchased from a number of suppliers including Osram-Sylvania. Advantageously, we have found that ultra-violet radiation operating predominantly at 254 nm can be used to inactivate typically over 99% of microorganisms in jet fuel, for example in JET A1 fuel. Significantly, we have found that ultra-violet radiation operating predominantly at 254 nm wavelength does not degrade or chemically alter the JET A1 fuel compositions under consideration.

The above and further features of the invention are set forth in the appended claims and will be explained in the following by reference to various exemplary embodiments and the specific Examples and Experiment which are illustrated in the accompanying drawings in which:

BRIEF DESCRIPTION OF THE DRAWINGS

FIG. 1 is a schematic view of a test rig designed and built at the BAE SYSTEMS Advanced Technology Centre, Filton;

FIGS. 3 and 4 are graphs showing the mean surface temperature profiles of UV bulbs as a function of time;

FIG. 6 is a graph of absorbance values, as obtained for four JET A1 samples (A, B, C, D), as a function of wavelength;

FIG. 7(b) is a cross-section view of an apparatus embodying the present invention;

FIG. 7(c) is a cross-section view of another apparatus embodying the present invention;

FIG. 8 is a graph showing the intensity profile of a UV bulb as a function of wavelength;

FIG. 14 is a perspective view of a surge tank apparatus; and

Table 1 is a summary table of operational data, as obtained for apparatus embodying the invention;

Table 2 is a summary table of dimensions of a test aircraft fuel line and flow rates;

Table 3 is a table of head height, as required to achieve maximum flow for a specified pipe diameter;

Table 4 is a table of frictional losses, as obtained for various lengths of a specified pipe diameter;

Table 5 is a summary table of temperature measurements, as recorded during simulated refuel conditions;

Table A is a table of aviation turbine fuels as used for powering gas turbine engine aircraft, and provides the designated specification for each fuel;

Table B is a summary table of UV dose values, as required to inactivate 99.9% of various known microorganisms;

Table C is a table of data, as obtained for four JET A1 samples (A to D) resulting from exposure of the samples to UV radiation (predominant wavelength 254 nm, power 28 mW/cm$^2$) over increasing exposure times; and Table C1 sets out percentage compositions of JET A1 samples A to D (as supplied by the University of West of England).

DETAIL DESCRIPTION OF EXEMPLARY EMBODIMENTS AND EXAMPLES

Product Concepts

For aircraft applications, the inventors have found that there are three potential locations where fuel sterilisation by means of ultra-violet irradiation can bring benefit:
1. An onboard fuel decontamination unit, where an ultra-violet sterilisation device is mounted in the aircraft fuel line.
2. An onboard surge tank unit which sterilises air and fuel vapours entering the fuel tanks of the unit.
3. A bowser mounted ultra-violet sterilisation unit in which fuel is treated by ultra-violet irradiation, rendering the fuel sterile as it is loaded on to the aircraft.

These three product concepts are described more fully hereinafter.

First Embodiment

Figure 7A:
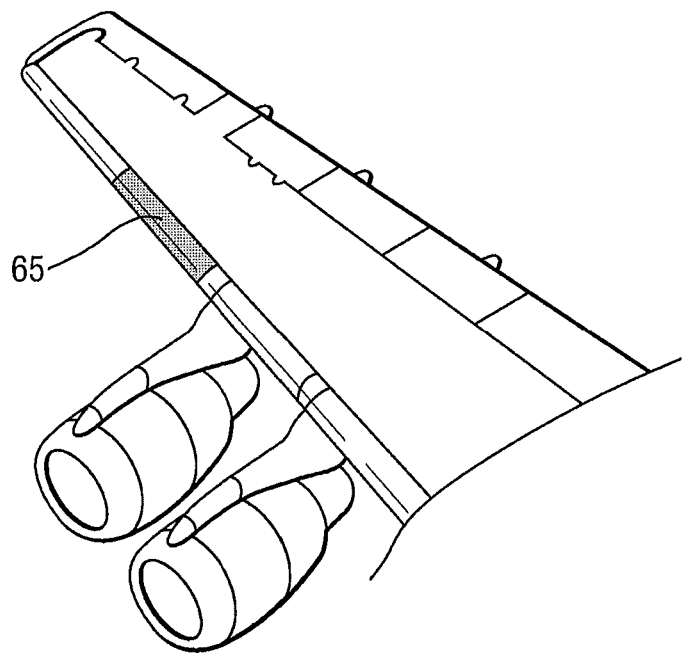
FIG. 7(a) is a schematic view of the position of a refuel panel on the underside of the leading edge of an aircraft wing.

Referring to FIG. 7(*b*), there is shown therein in cross-section view a preferred fuel decontamination apparatus 50 for use on an aircraft embodying the present invention. The apparatus 50 generally indicated in normal position, comprises a straight ultra-violet bulb 55 fitted and supported by supporting fins within a central straight section 56 of aircraft refuel pipe. The component dimensions (mm) are as marked on the Figure. The bulb is about 53.5 cm long. The bulb 55 and electrical wiring connections 57 are encased in a protective quartz sheath by a conventional process and as shown, the wiring connections are arranged to exit the pipe (see exit location 58) via an external elbow joint 62 on the outside of the fuel tank. The quartz sheath product is commercially available and can be obtained for example from Saint-Gobain (see link: www.quartz.saint-gobain.com). The front spar is represented as component 60 on the Figure. The bulb 55 in this embodiment is a Philips TUV PL-L 55 W HO low pressure mercury lamp with a predominant 254 nm wavelength output (see also the Philips UV lamp manufacturer's datasheet on the link: http://www.search.philips.com/search/isp/clickout.jsp?clicklocation=1&type=searchhit&text=UVC&section=lighting&locale=global&url=http://www.petrolstationlighting.com/gl_en/global_sites/application/water_purification/pdfs/uvp_air_water_brochure.pdf and the Experiment section). The generally Gaussian intensity profile 70 of the bulb is shown in FIG. 8.

The apparatus 50 is mounted on a bowser at location 59 by means of a bolting arrangement (not shown), and the wiring connections are connected externally to an electrical connector which in turn is connected to the refuelling panel (not shown in the FIG. 7). FIG. 7(*a*) shows the typical position of the refuelling panel in relation to the leading edge of an aircraft wing. As shown on the Figure in black section 65, the refuelling panel is located on the underside of the leading edge of the aircraft wing.

In operation of the thus described arrangement in this embodiment, it will be understood that JET A1 fuel, supplied by Air BP of Sunbury Business Park, Chertsey Road, Sunbury-upon-Thames, Middlesex, TW16 7LN, UK (see link: www.bp.com), of composition corresponding to designated specification ASTM D1655 (see the Example and Table A below) is passed through the aircraft refuel line and treated with UV radiation which is radiated by the bulb 55. The JET A1 fuel is exposed to the UV radiation for typically several minutes. (The fuel typically takes a second or so to flow across the apparatus.) In this embodiment, the UV radiation is directed in a direction substantially normal to the fuel flow direction (the fuel flow direction F is marked on the Figure). The optical power (UV dose) delivered typically at a 1 m distance from the bulb 55 is about 150 µW/cm$^2$ (refer to Philips TUV lamp manufacturer's datasheet). The JET A1 flow rate through the pipe is set at about 1250 L/min.

Note in this embodiment that at a JET A1 flow rate of 682 L/min, there is a calculated increased pressure drop (loss) of about 0.47 psi which is about 11% of the total pressure drop though the apparatus. At a JET A1 flow rate of 1250 L/min, there is a calculated increased pressure drop (loss) of about 1.4 psi, which is about 9% of the total pressure drop through the apparatus. These calculations are based upon the assumption that the bowser supplies at a continuous 50 psi pressure and does not compensate for the blockage in any way. (The inventors believe that there is evidence to suggest that the bowser automatically compensates for these losses.)

Second Embodiment

FIG. 7(*c*) shows another fuel decontamination apparatus 67 in cross-section view which is almost structurally identical to that described in the first embodiment of FIG. 7(*b*), but is configured to have a different wiring exit location such as to provide for the electrical wiring 57 to lie outside of the refuel line. FIG. 7(*c*) employs the same reference numerals as are employed in FIG. 7(*b*) for same/like parts. The component dimensions (mm) are as marked on the Figure.

Third Embodiment

Referring now to FIG. 9(*a*), there is shown therein in cross-section view another fuel decontamination apparatus 80 for use on an aircraft embodying the present invention. The apparatus 80 generally indicated in normal position, comprises a bespoke curved ultra-violet bulb 85 fitted within a central curved section 86 of aircraft refuel pipe. The component dimensions (mm) are as marked on the Figure. The bulb 85 is about 44.5 cm long. As shown, the bulb is encased within a protective curved quartz sleeve, supported by streamlined brackets or by other conventional means. Beneficially, the brackets are designed as small airfoils in order to minimise drag effects. The bulb operates at 54 W. The front spar is shown as component 79 on the Figure.

Figure 9A:
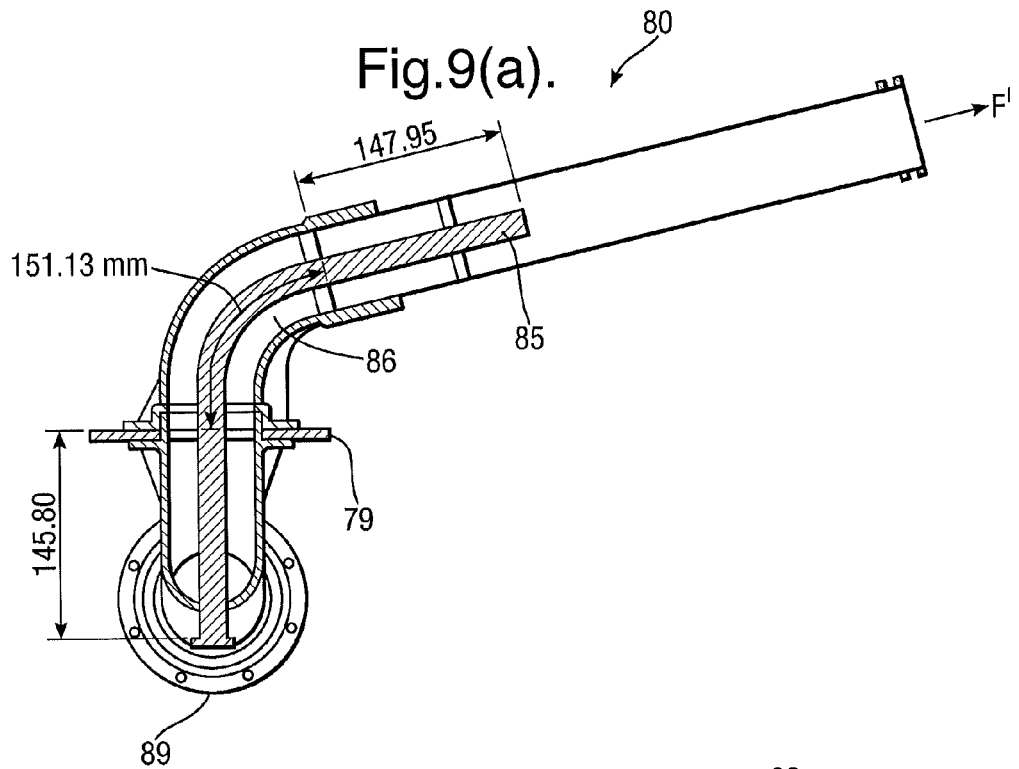
FIG. 9(a) is a cross-section view of another apparatus embodying the present invention.

The apparatus 80 of FIG. 9(a) is mounted on a bowser at location 89 by means of a bolting arrangement (not shown), and the wiring connections are connected to an electrical connector outside of the fuel tanks through an elbow joint. This apparatus thus provides a particularly convenient position for electrical connections, bearing in mind that the electrical connector is positioned next to the refuelling panel (not shown in the Figure).

In operation of the thus described arrangement in this embodiment, it will be understood that JET A1 fuel (the JET A1 fuel specification is as described in the first embodiment) is passed through the aircraft refuel line and treated with UV radiation which is radiated by the bulb 85. The JET A1 fuel is exposed to the UV radiation for typically one second or less.

As in the above described first embodiment, the UV radiation is directed in a direction substantially normal to the fuel flow direction (the fuel flow direction F' is marked on the Figure). The optical power (UV dose) delivered typically at a 1 m distance from the bulb is about 150 $\mu$W/cm$^2$. The JET A1 flow rate through the pipe is set at about 1250 L/min.

Note in this embodiment that at a JET A1 flow rate of 682 L/min, there is a calculated increased pressure drop (loss) of about 0.15 psi which is about 4% of the total pressure drop through the apparatus. At a JET A1 flow rate of 1250 L/min, there is a calculated increased pressure drop (loss) of about 0.4 psi which is about 3% of the total pressure drop though the system. As in the above described first embodiment, these calculations assume that the bowser supplies at a continuous 50 psi pressure and does not compensate for the blockage in any way.

Fourth Embodiment

Figure 9B:
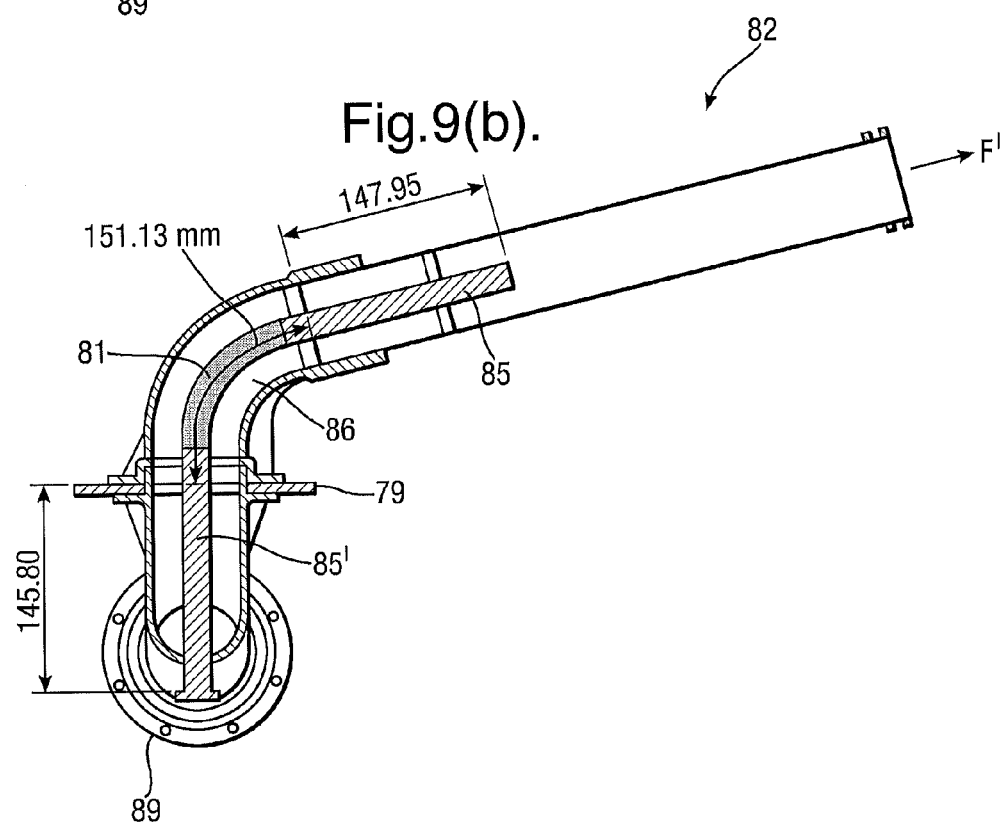
FIG. 9(b) is a cross-section view of another apparatus embodying the present invention.

FIG. 9(b) shows another fuel decontamination apparatus 82 in cross-section view which is almost structurally identical to that described in the third embodiment of FIG. 9(a), but is configured to have two separate, elongate bulbs 85, 85' separated by a space 81 within the U-shaped region 86 of the pipe. FIG. 9(b) employs the same reference numerals as are employed in FIG. 9(a) for same/like parts. The component dimensions (mm) are as marked on the Figure.

Fifth Embodiment

Figure 10:
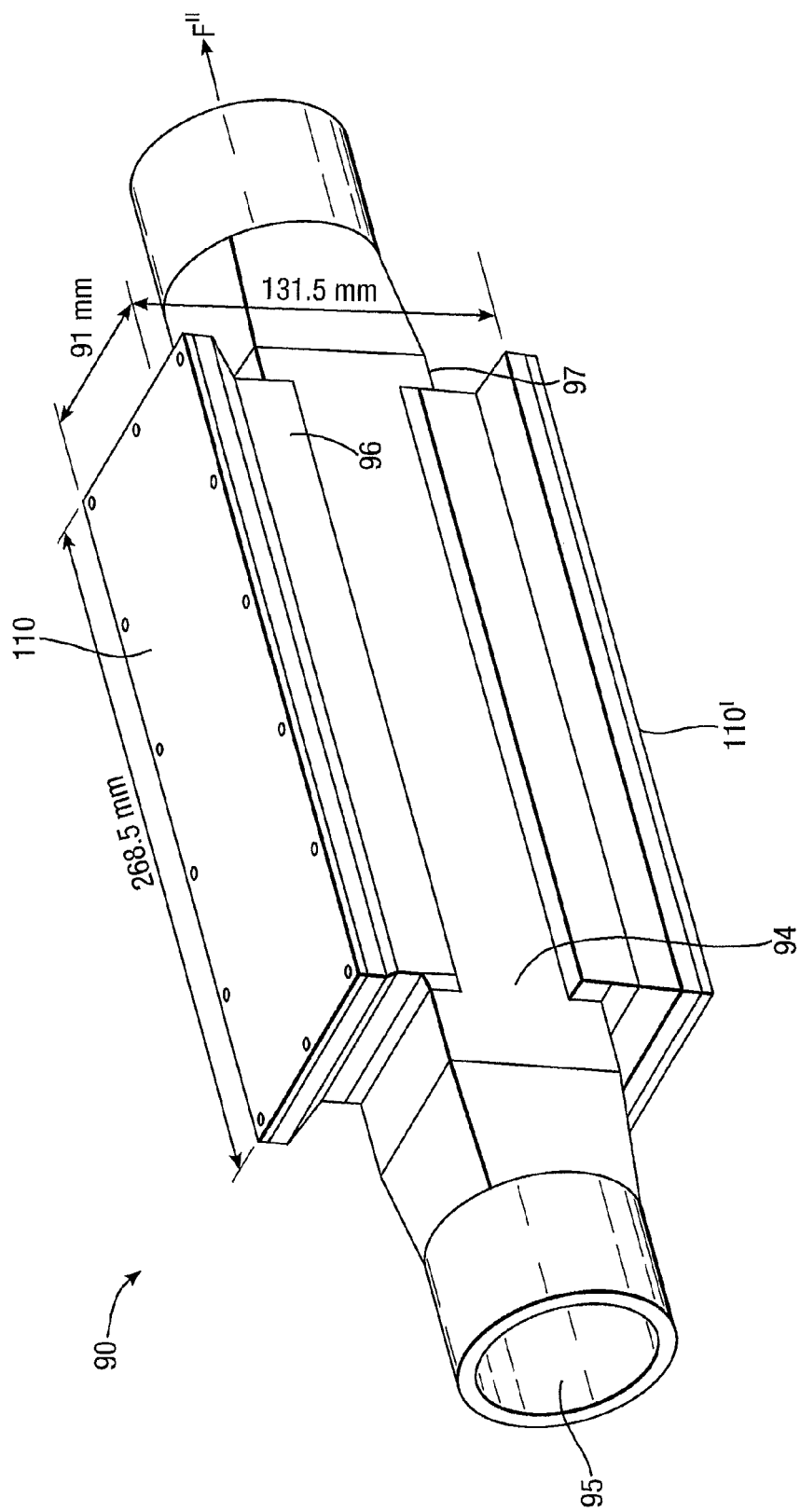
FIG. 10 is a perspective view of another apparatus embodying the present invention.

Referring now to FIG. 10, there is shown therein a perspective view of another preferred fuel decontamination apparatus 90 for use on an aircraft embodying the present invention. The apparatus 90 generally indicated in a horizontal normal position comprises a rectangular walled body portion 94 through which a tubular open ended duct 95 for channelling fuel flow is centrally formed. The body 94 of the apparatus is fitted with a UV-transparent window and UV bulbs at its upper 96 and lower 97 sidewalls (note that a protective cover 110, 110' is used to protect the windows and bulbs; whilst the windows and bulbs are not visible in this Figure, these can be seen clearly in FIG. 11(B)). Thus, in this embodiment, a UV unit is defined to replace a straight section of the refuel pipe, in which the UV-transparent windows and UV bulbs are positioned outside of the duct 95 such as to permit effective UV-irradiation of the fuel as it flows through the duct 95. The component dimensions (mm) are as marked on the Figure.

In this embodiment, the body 94 is formed of aluminium. Each bulb is about 22 cm long. Each bulb is a Philips TUV PL-L 35 W HO low pressure mercury lamp with a predominant 254 nm wavelength output (see also the Philips TUV lamp manufacturer's datasheet). The UV-transparent windows are formed of Spectrosil 2000 fused quartz manufactured by Saint-Gobain (see the link: www.quartz.saint-gobain.com with the product datasheets).

The apparatus 90 of FIG. 10 can be mounted on a bowser (not shown) by conventional means, and as described in the previous embodiments, the wiring connections are connected to an electrical connector outside of the fuel tanks (not shown in the Figure). Advantageously, the apparatus 90 is configured to provide a rigid, robust structure.

Figure 11A:
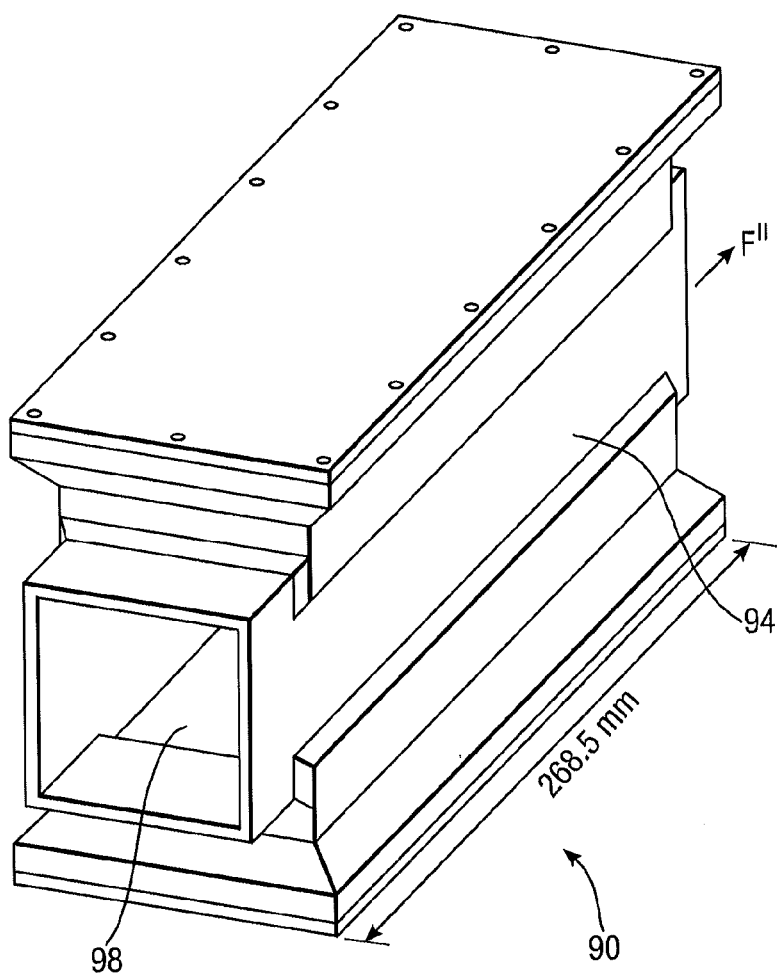
FIGS. 11(A) and 11(B) are cross-section views of the apparatus of FIG. 10.

FIG. 11(A) is a cross-section view of the apparatus of FIG. 10, and accordingly, like parts are given like reference numerals. As clearly shown, the body 94 of the apparatus 90 defines a rectangular walled duct of square cross-section 98 through which fuel is allowed to pass.

Figure 11B:
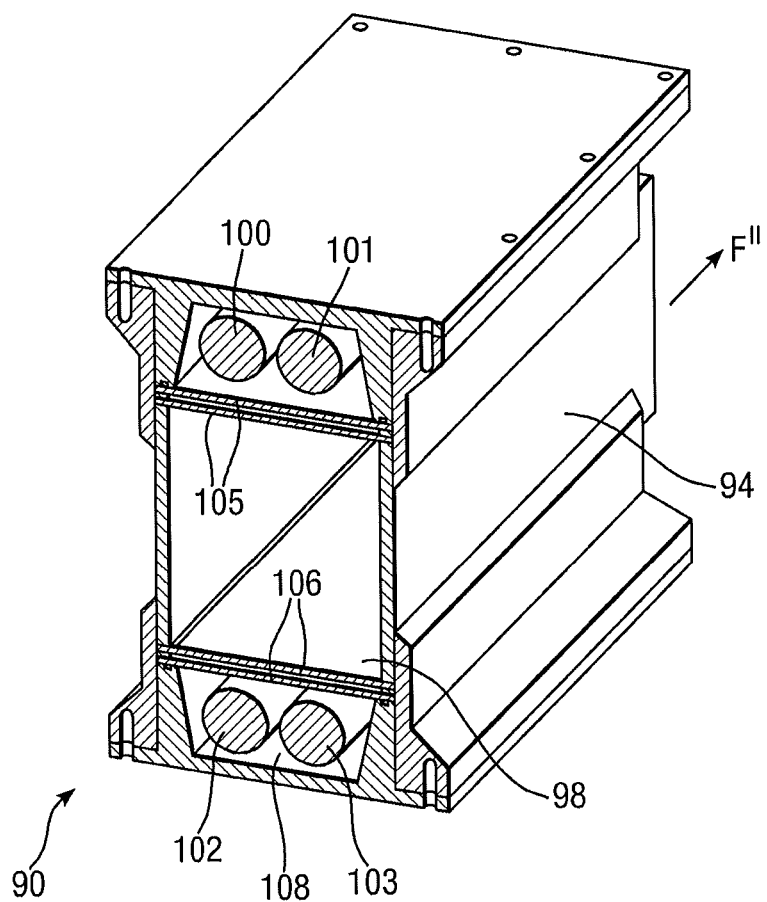

FIG. 11(B) is another cross-section view of the apparatus 90 of FIG. 10, and accordingly, like parts are given like reference numerals. FIG. 11(B) differs from FIG. 10 insofar as it shows the UV-transparent windows and the UV bulbs of the apparatus. As shown in the Figure, two UV bulbs 100, 101 are mounted in a first common plane, side-by-side, at an upper end of the apparatus 90, and additionally, two other UV bulbs 102, 103 are mounted in a second common plane, side-by-side, at an opposite, lower end of the apparatus. The two bulbs 100, 101 at the upper end are mounted above and carried by two sheets of UV-transparent quartz glass 105. The sheets of quartz glass 105 are positioned to separate the bulbs 100, 101 from the central duct region 98. The two bulbs 102, 103 at the lower end are mounted on a sidewall 108 of the apparatus and are separated from the central duct region 98 by two other sheets of UV-transparent quartz glass 106. Thus, the quartz glass sheets 105, 106 are positioned in this embodiment so that in use of the apparatus 90 UV radiation from the four bulbs 100, 101, 102, 103 is effectively directed at fuel flowing through the duct (via transmission by the quartz glass sheets) in a direction substantially normal to the fuel flow direction (the fuel flow direction F" is marked on the FIGS. 10, 11).

Note that in this embodiment the bulbs 100, 101, 102, 103 are supported at their ends using a suitable fuel-approved electrical potting compound (the potting compound is not shown in the Figure). We have found that a suitable potting compound that can be used for this purpose is PR1460Q-2 Potting Compound, obtainable for example from the link: www.silmid.com.

Figure 12:
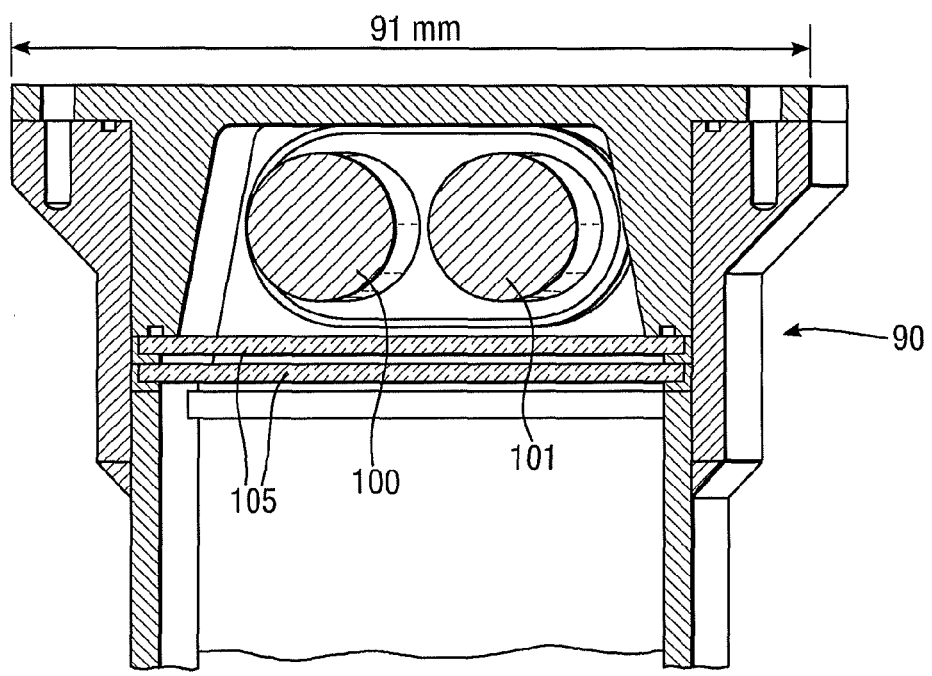
FIG. 12 is a cross-section view of the top half of the apparatus of FIG. 10.

FIG. 12 is a further cross-section view of the top half of the apparatus 90 of FIG. 10, and accordingly, like parts are given like reference numerals. As shown in the Figure, the two bulbs 100, 101 are mounted above the two sheets of quartz glass 105. As already mentioned, the bulbs are supported at their ends by use of potting compound (not shown in the Figure). The component dimensions (mm) are as marked on the Figure.

In operation of the thus described arrangement 90 in this embodiment, it will be understood that JET A1 fuel (the JET A1 fuel specification is as described in the previous embodiments) is passed through the aircraft refuel line and is effectively treated in the duct region of the apparatus with UV radiation by the UV unit of this embodiment. As already noted above, the UV radiation is directed at the fuel in a direction substantially normal to the fuel flow direction F'" (see FIGS. 10, 11). The optical power (UV dose) delivered typically at 1 m distance from the bulbs of the apparatus is about 105 $\mu$W/cm$^2$. The JET A1 flow rate through the duct is set at about 1250 L/min.

Advantageously, the UV unit of this embodiment is modular and if desired for example, several such units can be installed on aircraft in parallel or in series to treat aviation fuel.

Sixth Embodiment

Figure 13A:
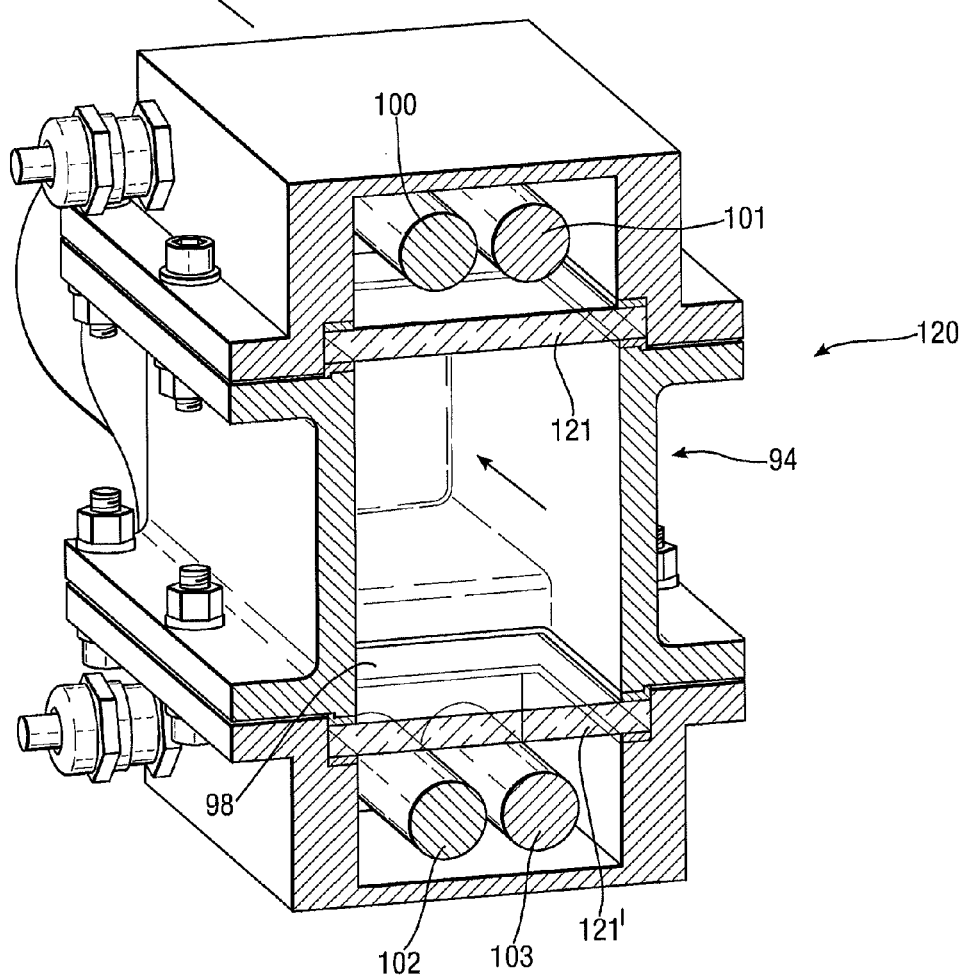
FIG. 13(a) is a perspective view of another apparatus embodying the present invention.

This apparatus 120 is shown in perspective view in FIG. 13(a). This is as in the above described fifth embodiment (like parts are given like reference numerals), except that instead of using a double layer of quartz glass in each window, a single layer of high grade thick Spectrosil fused quartz glass 121, 121' (see the link: www.quartz.saint-gobain.com with the product data sheets) is used in each window to protect the bulbs from the fuel as it flows through the duct 98.

Figure 13B:
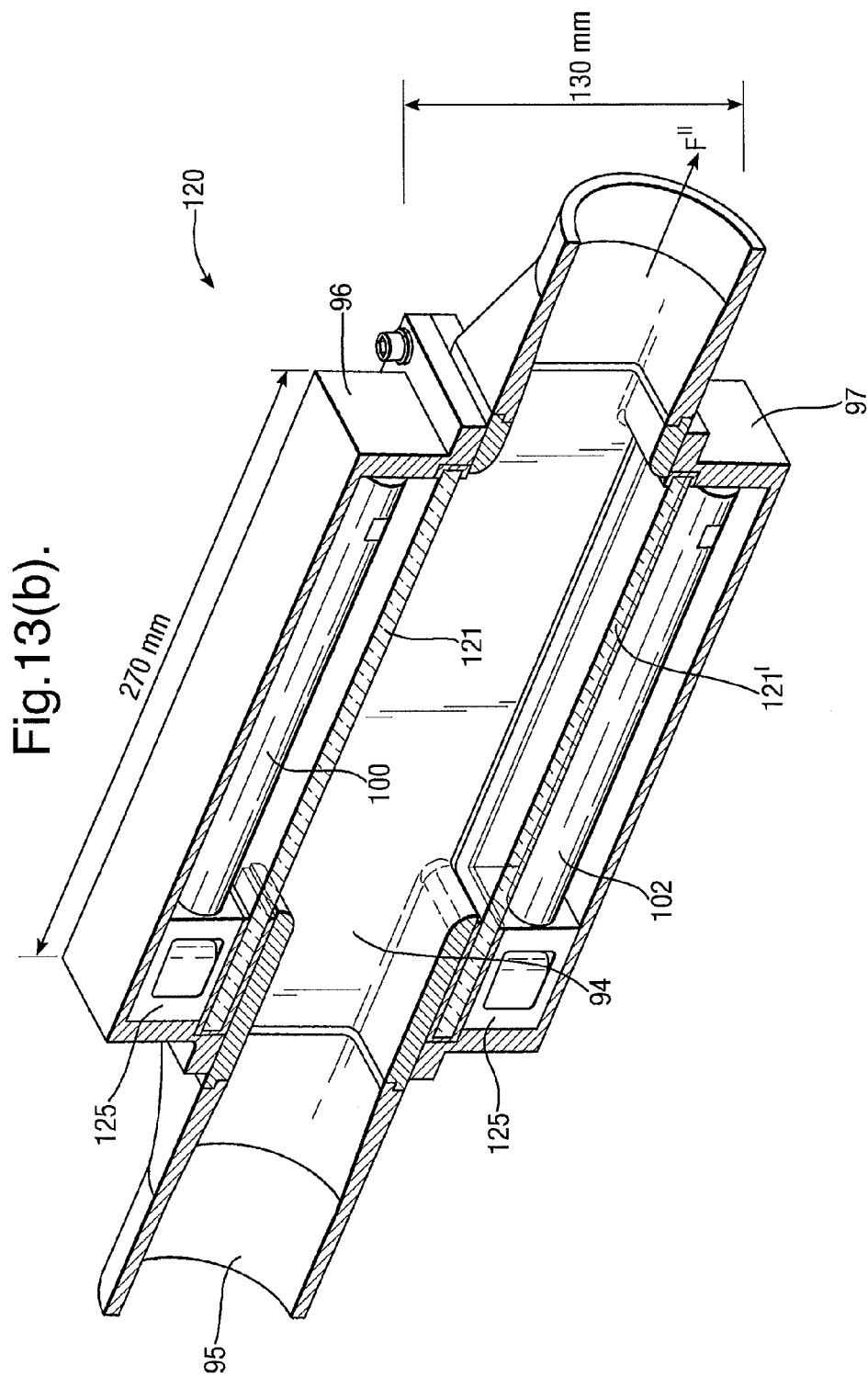
FIG. 13(b) is a cross-section view of the apparatus of FIG. 13(a)

FIG. 13(b) is a further cross-section view of the apparatus 120 of FIG. 13(a), and accordingly, like parts are given like reference numerals. As shown in the Figure, one half of the body interior 94 includes a centrally-formed section of the duct 95 with one elongate UV bulb 100 mounted outside of the duct at an upper side 96 and another elongate UV bulb 102 mounted outside of the duct at an opposing lower side 97. Each bulb is shown to extend in a direction generally parallel to the direction of fuel flow F'" along the duct. As also shown, each bulb is separated from the duct region by UV-transmissive quartz glass 121, 121'. Component dimensions (mm) are as marked on the Figure.

As also shown in FIG. 13(b), each bulb 100, 102 is supported at its ends using fuel-approved electrical potting compound 125 (potting compound details are as in the above described fifth embodiment) with gasket seal in place.

Seventh Embodiment

As in the above described fifth embodiment, except that instead of irradiating the fuel by using UV bulbs at upper and lower locations, only the UV bulbs at the upper location are used to treat the fuel. Thus, in this embodiment, the fuel is irradiated by the bulbs from the upper side only and there are no bulbs present at the lower side.

Eighth Embodiment

As in the above described fifth embodiment, except that instead of irradiating the fuel by using UV bulbs at upper and lower locations, only the UV bulbs at the lower location are used to treat the fuel. Thus, in this embodiment, the fuel is irradiated by the bulbs from the lower side only and there are no bulbs present at the upper side.

Ninth Embodiment

UV Sterilisation of Vent Air

The source of microbial contamination is predominantly the fuel, but atmospheric air carrying flammable materials, which enters the aircraft fuel tanks as the fuel is used or drained may also carry organisms in with it.

FIG. 14 is a perspective view of a surge tank apparatus 130 on an aircraft in which air is allowed to enter the tanks through a National Advisory Committee for Aeronautics (NACA) duct 131, as mounted within the surge tank of each wing of the aircraft. (NACA duct pressure data: the pressure created in the wing tanks is about $5.14 \times 10^{-3}$ psig and $7.10 \times 10^{-3}$ psig in the central tank for the worst case where air (hence microorganisms) is sucked into the tank at a maximum rate of descent of 10000 ft/min). For NACA duct description see the link http://en.wikipedia.org/wiki/NACA_duct.

Referring again to FIG. 14, the apparatus 130 generally indicated in normal position further includes a UV irradiation unit 132 mounted on rib 19 (by using brackets attached to rib) at one side of the apparatus. The UV irradiation unit 132 comprises a UV bulb (Philips TUV 25 W bulb, and refer to the manufacturer's datasheet), with 45° solid quartz lens 135 (supplier: Saint-Gobain—see previously described embodiments), encased within a spark proof housing. The lens is oriented such that the normal to the lens surface is at about 45° to the direction of the incident UV beam. As shown in the Figure, the UV irradiation unit is configured and mounted above an existing support joist such that, in use of the apparatus, UV light emitted by the UV bulb of the UV irradiation unit 132 is directed downwards by the 45° solid quartz lens 135 onto a reflective plate 136 which is located at the bottom of the tank and then the light in turn is reflected directly under the exposed vent pipes 137, 137', 137". One advantage of such a mounting arrangement 130 is that the vent pipes 137, 137', 137" are effectively exposed to the UV radiation in the sense that all air entering the tanks is UV treated. In other embodiments, the orientation of the lens can be varied, as can the locations of the UV irradiation unit and the reflective plate.

Any possible interference between the air to be UV treated and the UV-irradiation mounting unit is thus avoided in this embodiment.

Another advantage is that the described arrangement of FIG. 14 is robust.

Figure 15:
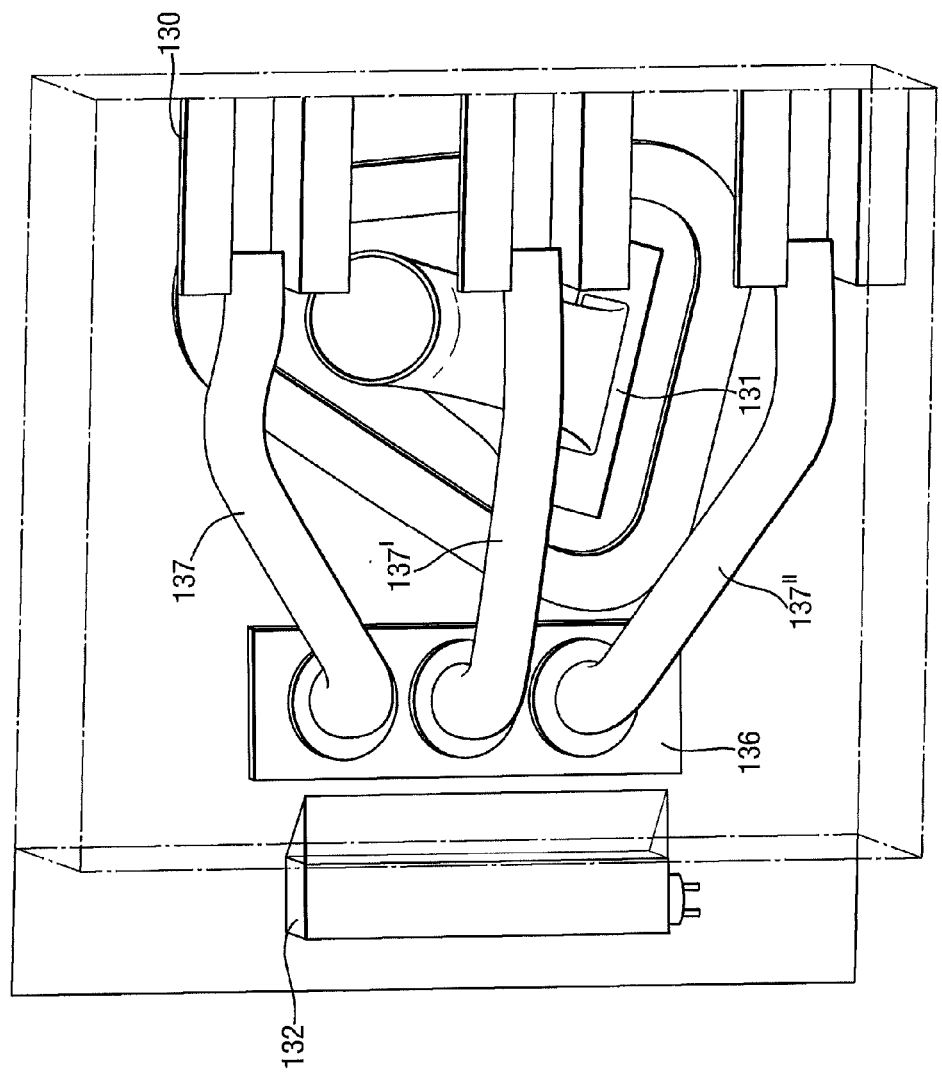
FIG. 15 is a top plan (birds-eye) view of the apparatus of FIG. 14.

FIG. 15 is a plan (birds-eye) view of the surge tank apparatus 130, with the proposed UV irradiation unit 132 fitted at one side, and accordingly, like parts are given like reference numerals.

It is to be further appreciated that the above described UV irradiation unit could be mounted in other different locations within the surge tank, if desired. Additional UV irradiation units with, optionally, additional reflective plates of the above described kind could also be incorporated at different locations within the surge tank, if desired. In an alternative embodiment, the inventors envisage that the above described UV irradiation unit could be fitted to the rear spar, exposing the vent pipe outlets from the side. Whilst an advantage of such an arrangement is that interference between the air to be UV treated and the UV-irradiation mounting unit is avoided, it is recognised that irradiation of the air may be significantly less efficient than that achieved using the above described embodiment of FIG. 14.

UV Sterilisation Unit Mounted on the Refuel Platform

There are three types of refuelling vehicle; fuel tanker (also known as a surface refueller or bowser), hydrant vehicle and a hybrid vehicle, which is a combination of both. The latter is not common and is not currently found in the UK. In each instance the principles of operation are similar and all that is required here is an indication of flow rate, pressure and power source.

One difference between tankers is fuel capacity. This varies from 20 to 45,000 liters (max in UK). The size and design of the pump systems also vary as do the coupling and availability of space.

The output pressure of an Air BP tanker is typically 80 psi; however, this is automatically reduced via an internal pressure gauge which tailors the pressure to that certified for a specific aircraft. In the case of one test aircraft, this is 50 psi. The main source of electrical power is the diesel engine, providing 24V DC to the pump.

The hydrant vehicle, also called a dispenser or cart, does not possess a fuel tank or pump. Instead, it is used to manage fuel taken from a central airport reserve, which is piped from beneath the parking apron. The vehicle is fitted with fuel filters, pressure controller, meter and elevating platform (to allow the operator to reach the refuel point under the wing). The vehicle may be diesel, electrical or a towed platform and again has a 24V DC supply. The attached hose is about 12 meters long (100 mm ID; BDV-100C type) and the hydrant divides the flow through two smaller hoses.

We have found that there is a number of places where an in-line UV unit of the type described in the previously described embodiments could be fitted on any of the above-mentioned fuel platforms. One place for fitting could be after the filters and prior to the flexible hose. The difficulty here is recognised to be efficient irradiation, because the pipe is of considerable diameter (between 50-100 mm ID) and the flow rate is considerably higher (maximum of typically 4500 L/min). In order to sterilise efficiently the fuel, it is envisaged that the flow may have to be split into a number of smaller diameter pipes. This could reduce the problem of light attenuation. A combination of higher power bulbs and/or longer exposure times could then be used when refuelling at high flow rates.

Furthermore, in realising the concept of using ultra-violet (UV) light to sterilise aircraft fuel, the inventors have recognised and have had to address several fundamental questions. As will be described in the following sections hereinafter, these include technical questions over UV bulb temperature, fuel flashpoint and the effect of ultra-violet light on the chemical composition of kerosene-based (jet) fuels under consideration.

Aviation Turbine Fuel (AVTUR)

The following types of kerosene fuel were approved for use on test aircraft (See Table A). Jet A and Jet A1 are the most commonly used fuels. Refer also to the data sheets for aircraft fuel for jet engines and rotary engines which can be found on the link: http://en.wikipedia.org./wiki/Aviation_fuel.

TABLE A

Aviation turbine fuels used for powering gas turbine engine aircraft and the designated specifications for each.

| | Description: | Flash Point: | Specification: |
|---|---|---|---|
| Jet A1 | Civil grade fuel used worldwide, outside of North America and the former Soviet Union. | 38° C. | DEF STAN 91-91 ASTM D1655 (JET A1) |
| Jet A | Civil grade fuel supplied at airports throughout USA and parts of Canada. | 38° C. | ASTM D1655 (JET A) |
| Jet TS-1 | Civil grade fuel supplied within the former Soviet Union and in some E. European countries, although Russian production is now rapidly switching to Jet A1. | 28° C. | GOST 10227 |
| JP-8 | Military equivalent of Jet A-1 with corrosion inhibitor and anti-icing additives | 38° C. | DEF STAN 91-87 MIL-DTL-83133 |
| JP-5 | High flashpoint kerosene used by the Navy | >60° C. | DEF STAN 91-86 MIL-DTL-5624. |

Flammability

Flashpoint is the lowest temperature at which a substance can form an ignitable mixture in air and requires an ignition source (flame, spark). At this temperature the vapour may cease to burn when the source of ignition is removed.

The auto-ignition point is the lowest temperature at which a substance will spontaneously ignite without an ignition source and in normal atmospheric conditions. For AVTUR fuel types this is between 210-240° C. Please note, however, that a value of 200° C. is given in EU airworthiness codes (EASA CS-25.863).

The temperature of all experimental equipment was monitored closely and recorded throughout experiments. It was not envisaged that any equipment or exposed UV source would exceed 65° C. In these instances, all sources of ignition were isolated from the fuel, and all experiments were carried out in accordance with safety regulations.

Fuel Additives

Aviation fuel additives are compounds added to kerosene. Typically, these are present in small amounts; parts per million. Each fuel standard specifies which additives can be present and the maximum concentration permitted (Table A); however, the precise composition will vary from fuel supplier and between batches. Common additives include a range of antioxidants, MDA metal deactivator, Stadis 450 static dissipater, LIA lubricity improver, FSII icing inhibitor and a leak detection additive. The list of approved additives tested is included in Def Stan 91-91 Annex A and ASTM D1655 Table A (see above).

Chemical analysis of Jet A1, with its associated additives, was further conducted to ensure that UV irradiation was not damaging to the total fuel composition (see following section).

Electrical Power Limits

It was found that there was no specific limitation as to what the maximum level of electrical power could be within the aircraft. The basic aircraft power source is 3 phase 400 Hz at 200V across phases, and 115V 400 Hz between phase and neutral. From this, 26V AC (400 Hz) is also available. A 28V DC supply is also available from the Transformer Rectifier Unit (powered from the AC supply) or batteries. We have used the 115V AC supply.

Experiment

Recorded Bulb Temperature

Figure 2A:
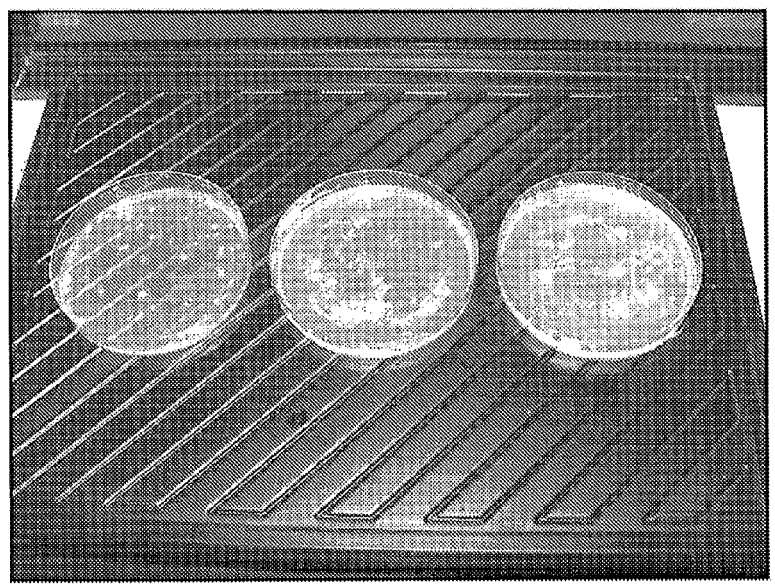
FIGS. 2A to 2E are photographic images of plates having UV irradiated samples, with the level of contamination shown to be progressively increased from FIG. 2A to 2E.
Figure 2B:
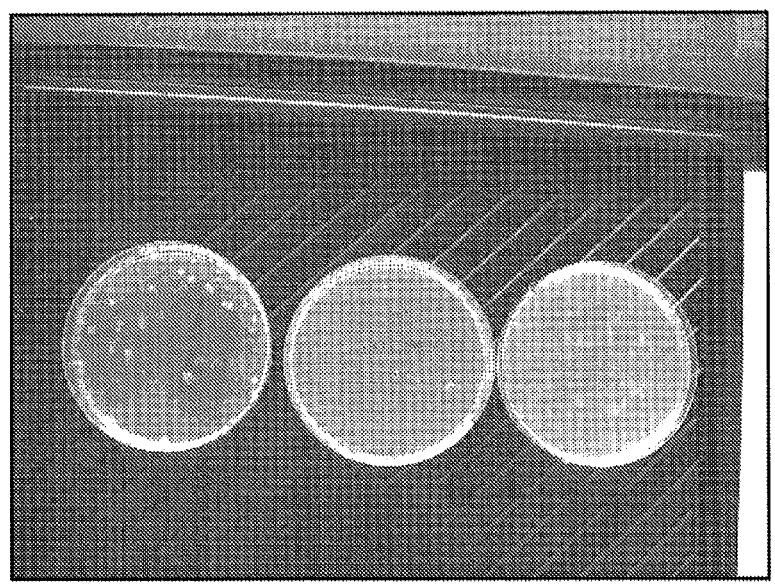
Figure 2C:
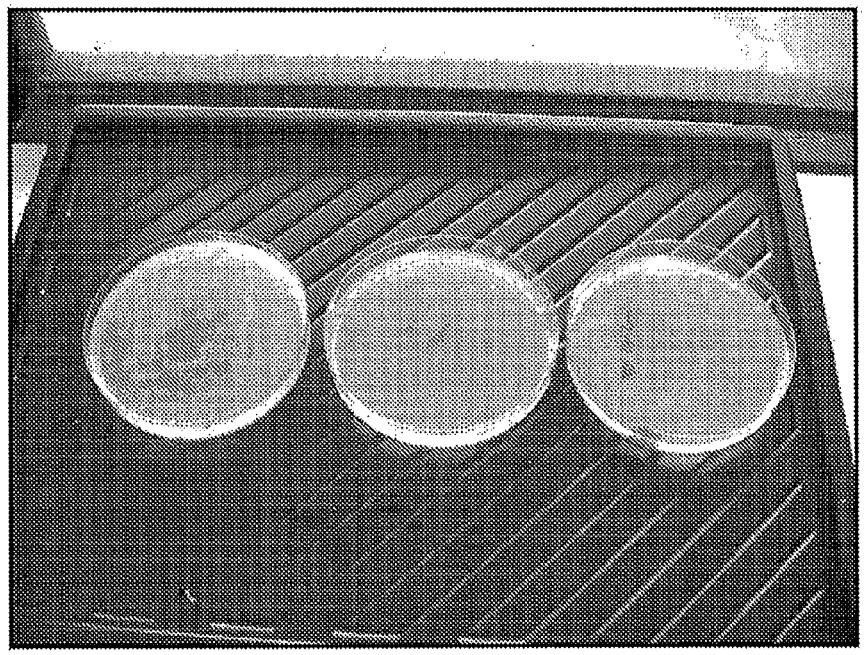
Figure 2D:
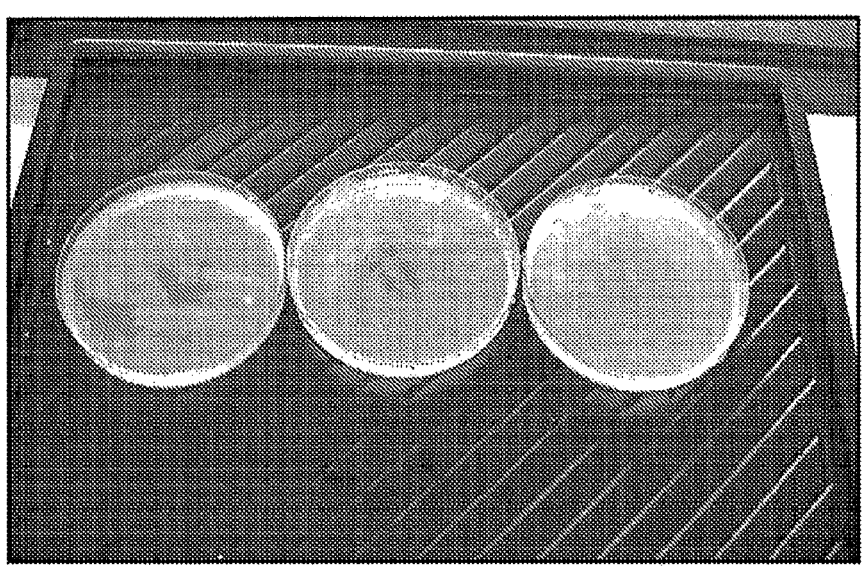
Figure 2E:
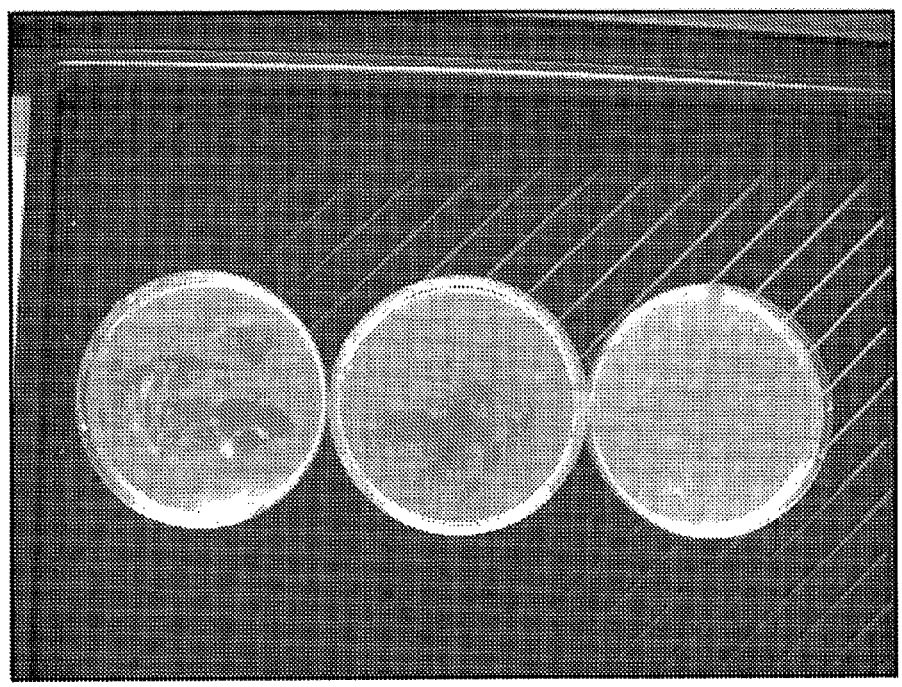
Figure 5:
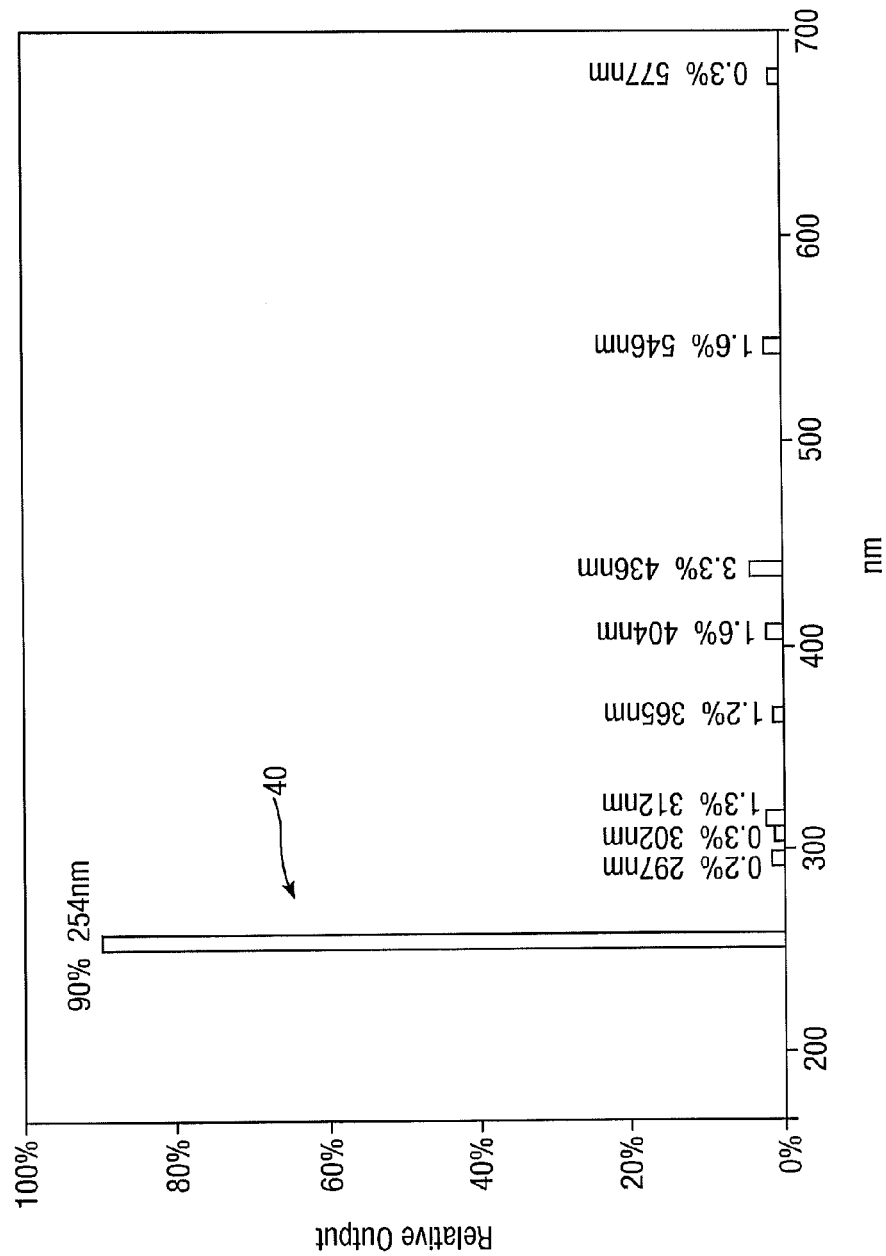
FIG. 5 is a graph of the output of a UV bulb operating predominantly at 254 nm wavelength.

The surface temperature of two UV-C bulbs was recorded by placing calibrated thermocouples to the surface of two UV-C bulbs at their centres and tested separately. Each bulb was a Sylvania G4 W UV-C low pressure mercury bulb, which is known to have a predominant 254 nm wavelength output 40 (refer to FIG. 5 and to the Osram-Sylvania product sheet FL-UVC002R1). This experiment was conducted in air and all other bulbs were subject to this same test prior to further experimentation.

Bulb temperatures were recorded at 5 second intervals for a total of 3 hours. The typical mean surface temperature profile of the bulbs as a function of time 35, 36 is shown in FIGS. 3 and 4.

Bulbs of other different powers were tested (e.g. at operating powers of 36 W, 55 W), and the recorded bulb temperatures were found to be significantly lower than the auto-ignition point.

Optical Power

The optical power of the bulbs was characterised with reference to the manufacturer's technical specifications, in particular with respect to the UV dosage.

The optical power of Sylvania G4 W UV-C bulbs for example was characterised using a UV-C light detector. The detector was placed 2 cm beneath the surface of the bulb and measurements recorded within a shielded light box. The recorded optical power at a 2 cm distance from the bulbs in air was 28,000 $\mu W \cdot sec/cm^2$. Table B provides an indication of the optical powers required to kill numerous microorganisms. Specifically, we are interested in the *Bacillus* species as they have been shown to corrode aluminium and *Penicillium* species as they have been isolated from JP8.

TABLE B

UV dose (µW · sec/cm$^2$) required to inactivate 99.9% of various microorganisms (not fuel specific).

| Microorganism | UV dose |
|---|---|
| Bacteria | |
| Agrobacterium tumefaciens | 8 500 |
| Bacillus anthracis | 8 700 |
| Bacillus megatherium | 2 500 |
| Bacillus subtilis | 11 000 |
| Clostridium tetani | 23 100 |
| Clostridium botulinum | 11 200 |
| Corynebacterium diphtheria | 6 500 |
| Dysentery bacilli | 4 200 |
| Eberthella typhosa | 4 100 |
| Escherichia coli | 6 600 |
| Legionella bozemanii | 3 500 |
| Legionella pneumophila | 12 300 |
| Micrococcus candidus | 12 300 |
| Mycobacterium tuberculosis | 10 000 |
| Neisseria catarrhalis | 8 500 |
| Phytomonas tumefaciens | 8 500 |
| Proteus vulgaris | 6 600 |
| Pseudomonas aeruginosa | 10 500 |
| Pseudomonas fluorescens | 6 600 |
| Rhodospirillum rubrum | 6 200 |
| Salmonella paratyphi | 6 100 |
| Salmonella typhi | 7 000 |
| Serratia marcescens | 6 160 |
| Shigella dysenteriae | 4 200 |
| Shigella flexneri | 3 400 |
| Spirillum rubrum | 6 160 |
| Staphylococcus aureus | 6 600 |
| Staphylococcus epidermidis | 5 800 |
| Streptococcus faecaila | 10 000 |
| Streptococcus pyrogenes | 4 200 |
| Streptococcus viridans | 3 800 |
| Vibrio cholerae | 6 500 |
| Molds | |
| Aspergillus flavus | 99 000 |
| Aspergillus glaucus | 88 000 |
| Aspergillus niger | 330 000 |
| Mucor mucedo | 77 000 |
| Oospora lactis | 11 000 |
| Penicillium chrysogenum | 56 000 |
| Penicillium digitatum | 88 000 |
| Penicillium expansum | 22 000 |
| Rhizopus nigricans | 220 000 |
| Protozoa | |
| Chlorella vulgaris | 22 000 |
| Blue-green algae | 420 000 |
| Giardia lamblia | 100 000 |
| Nematode eggs | 40 000 |
| Paramecium | 200 000 |
| Virus | |
| Bacteriophage | 6 600 |
| Infectious hepatitis | 8 000 |
| Influenza | 6 600 |
| Rotavirus | 24 000 |
| Tobacco Mosaic | 440 000 |
| Yeasts | |
| Baker's yeast | 8 800 |
| Brewer's yeast | 6 600 |
| Common yeast cake | 13 200 |
| Saccharomyces cerevisiae | 13 200 |

Reference for Table B is as follows: -
Title: UV Technologies in Water Purification Systems
Author/s: Ichiro Kano, Daniel Darbouret & Stéphane Mabic (Millipore)
Reference: The R&D Notebook No. RD009
Affiliation: Millipore Corporation
Address: Research & Development, Laboratory Water Division, Millipore S.A., St. Quentin-en-Yvelines, France
Description: Product/Technology Review
Water System: Milli-Q, Elix & RiOs systems and storage reservoirs
http://www.millipore.com/bibliography.nsf/a73664f9f981af8c852569b9005b4eee/5098cca75b95918f85256ced00549922/$FILE/RD009.pdf UV Irradiation of JET A1

This investigation was focused only on UV irradiation and analysis of Jet A1. Tests were subsequently conducted on other fuel variants.

To examine the effects of UV wavelengths on the chemical composition of Jet A1 fuel, controlled amounts of fuel were irradiated for a timed duration and then analysed (results presented in following section). Small 4.5 ml quantities of Jet A1 were placed within quartz cuvets, suitable for the transmission of short UV wavelengths. Each cuvet was then mounted 2 cm beneath a Sylvania G4 W UV-C bulb and irradiated at 28 mW·sec/cm$^2$ within a shielded light box. This experiment was also conducted in a fume cabinet to reduce the concentration of fuel vapours. A total of four samples, including a control, were prepared for analysis (see Table C below).

TABLE C

Jet A1 samples exposed to wavelength (λ) 254 nm at a power of 28 W/cm$^2$ for increasing time periods.

| Sample: | Exposure Time: | Description: |
|---|---|---|
| A | Zero | Control: Fuel placed in cuvet but not exposed to UV. |
| B | 2 seconds | Predicted exposure time within rig. |
| C | 1 minute | Prolonged exposure |
| D | 10 minutes | Maximum exposure |

The percentage composition of JET A1 for each of the samples A, B, C, D is further provided in Table C1 below.

The following methods of analysis were then used to examine whether 254 nm wavelength UV-irradiation had any effect on the chemical composition of Jet A1.

Analysis

A number of analysis methods, as set out, were used to quantify the effect of a 254 nm wavelength on the chemical composition of JET A1 and the additives commonly found within it. In each instance the control sample (A) was compared against the treated samples (B, C and D).

UV/VIS Spectrophotometry

As will be appreciated by the skilled person in the art, ultraviolet-visible spectrophotometry uses light in the visible and near ultraviolet range to quantitatively determine the composition of solutions. This method is suited to solutions containing highly conjugated organic compounds, because they absorb light in this region. Values are given in absorbance (abs) and this is determined as:

$$abs=\log_{10}(I_0/I),$$

where I is the intensity of light that has passed through the sample (transmitted light intensity) and $I_0$ is the intensity of the light before it enters the sample.

FIG. 6 is a plot 45 of the absorbance values for all four JET A1 samples (A, B, C, D) as a function of wavelength. The Figure shows that all four samples follow the same trendline, further indicating that there is no significant change in overall composition of JET A1. The graph 45 also shows standard error bars for the non-exposed sample A. This shows that sample C falls within the error range. At shorter wavelengths (<300 μm) both sample B and D are outside the error bars. However, these are either side of sample A; therefore indicating no consistency. When error bars are included for all data points there is a clear overlap between all 4 samples.

GC-MS

As will be appreciated by the skilled person in the art, this method combines Gas Chromatography and Mass Spectrometry (GC-MS). A gas chromatograph is first used to separate the different molecules in a mixture, which then allows the mass spectrometer to evaluate the constituent molecules individually.

TABLE C1

GC-MS data showing percentage composition of Jet A1.

| Identified Compounds | % Composition | | | | Normalised Data (n) | | | | | | | | | |
|---|---|---|---|---|---|---|---|---|---|---|---|---|---|---|
| | A | B | C | D | A | n | B | n | C | n | D | n | Range | Difference |
| octane | 4.25 | 4.6 | 3.7 | 4.5 | 4.25 | 6.8 | 4.6 | 7.4 | 3.7 | 6.4 | 4.5 | 7.1 | 0.7 | −0.3 |
| p-xylene | 4.95 | 4.5 | 3.4 | 4.2 | 4.95 | 8 | 4.5 | 7.3 | 3.4 | 5.9 | 4.2 | 6.6 | 2.1 | 1.3 |
| nonane | 4.4 | 4.65 | 4.5 | 4.5 | 4.4 | 7.1 | 4.65 | 7.5 | 4.5 | 7.8 | 4.5 | 7.1 | 0.7 | −0 |
| 3-et-2-me-heptane | 2.8 | 3.1 | 2.6 | 2.8 | 2.8 | 4.5 | 3.1 | 5 | 2.6 | 4.5 | 2.8 | 4.4 | 0.1 | 0.1 |
| 1-et-3-me-benzene | 4.9 | 4.95 | 4.6 | 4.9 | 4.9 | 7.9 | 4.95 | 8 | 4.6 | 8 | 4.9 | 7.7 | 0.3 | 0.1 |
| 4-et-octane | 3.3 | 3.6 | 3.25 | 3.5 | 3.3 | 5.3 | 3.6 | 5.8 | 3.25 | 5.6 | 3.5 | 5.5 | 0.3 | −0.2 |
| 1-et-2me-benzene | 3.3 | 3.3 | 2.8 | 3.25 | 3.3 | 5.3 | 3.3 | 5.3 | 2.8 | 4.9 | 3.25 | 5.1 | 0.4 | 0.2 |
| 1,3,5-trime-benzene | 5.2 | 5.2 | 4.7 | 5.1 | 5.2 | 8.4 | 5.2 | 8.4 | 4.7 | 8.2 | 5.1 | 8.1 | 0.3 | 0.3 |
| 1-me-3-pr-benzene | 3.4 | 3.55 | 3.4 | 3.7 | 3.4 | 5.5 | 3.55 | 5.7 | 3.4 | 5.9 | 3.7 | 5.8 | 0.4 | −0.4 |
| 1-me-4-i-pr-benzene | 4.4 | 4.3 | 4.3 | 4.6 | 4.4 | 7.1 | 4.3 | 7 | 4.3 | 7.5 | 4.6 | 7.3 | 0.4 | −0.2 |
| 1,2,3,5,tetme-benzene | 3.4 | 3.2 | 3.2 | 3.6 | 3.4 | 5.5 | 3.2 | 5.2 | 3.2 | 5.6 | 3.6 | 5.7 | 0.2 | −0.2 |
| 1-me-3,5-diet-benzene | 3.4 | 3.1 | 3.1 | 3.6 | 3.4 | 5.5 | 3.1 | 5 | 3.1 | 5.4 | 3.6 | 5.7 | 0.3 | −0.2 |
| 3-me-undecane | 4.1 | 4.1 | 4.1 | 4.3 | 4.1 | 6.6 | 4.1 | 6.6 | 4.1 | 7.1 | 4.3 | 6.8 | 0.5 | −0.2 |
| 2,6-dime-undecane | 4.6 | 4.55 | 4.6 | 4.75 | 4.6 | 7.4 | 4.55 | 7.4 | 4.6 | 8 | 4.75 | 7.5 | 0.6 | −0.1 |
| 2,6,10-trime-tetdecane | 3.6 | 3.2 | 3.4 | 3.7 | 3.6 | 5.8 | 3.2 | 5.2 | 3.4 | 5.9 | 3.7 | 5.8 | 0.1 | −0.1 |
| 3-me-tetradecane | 2.2 | 1.9 | 2 | 2.3 | 2.2 | 3.5 | 1.9 | 3.1 | 2 | 3.5 | 2.3 | 3.6 | 0.1 | −0.1 |
| SUM | 62.2 | 61.8 | 57.7 | 63.3 | | | | | | | | | | |

Normalised data calculated as a division of 1% of the sum.

This data and calculations were supplied by University of West of England and in their opinion show no significant difference between samples.

EXAMPLE

In-Line Fuel Decontamination

In order to validate the concept of using short UVC light to sterilise flowing aviation fuel, an experimental gravity fed test rig was designed and built at the BAE SYSTEMS Advanced Technology Centre, Filton. The proposed testing design parameters have been set out hereinafter in sections A1. and A2. Its purpose was to simulate the refuel conditions of a test aircraft; specifically the velocity range that occurred during refuelling (as explained hereinafter in section A2.). The rig was fitted with a UV sterilisation unit, of the type described above in the sixth embodiment developed by BAE SYSTEMS (see Table 1).

TABLE 1

| Dimensions: | 270 × 90 × 130 mm |
|---|---|
| Dimensions of window glass: | Two of 245 mm × 67 mm × 6.5 mm thick (Spectrosil 2000) |

TABLE 1-continued

| Operational pressure: | 50 psi (maxium 180 psi) |
|---|---|
| Fuel Pipe Connection: | 2.5" |
| Lamps inside: | 2 × 38 W (Phillips TUV PL-L35W HO) |
| Electrical Power Supply: | 230-240 V |
| Control Gear: | ECG (Osram Electronic Control Gear) |

Optical Output

The electrical consumption of a bulb, i.e. wattage, provides an indication of optical output, but does not directly state the optical density. In order to develop a better understanding of the kill efficiency it is necessary to measure this directly. An OPHIR meter, specifically for ultra-violet (UV) wavelengths was used to measure the optical power output (refer to manufacturer's datasheet).

A1. Test Rig

The gravity fed test rig was built in a peripheral laboratory at the BAE SYSTEMS Advanced Technology Centre, Filton site. The rig was fitted with an industrial ventilation system suitable for the removal of ignitable fumes. FIG. 1 is a schematic view of the test rig 20. As shown in the Figure, the test rig 20 in its normal position comprises a header tank 21 at its upper end, an ultra-violet sterilisation unit 22, and a collection tank 23 at its lower end. The ultra-violet sterilisation unit 22 is mounted at a position between the header tank 21 and the collection tank 23 by means of a conventional pipe arrangement formed of stainless steel, with compression fittings 24, and with nozzle attachments 26 between the pipe and the ultra-violet sterilisation unit. As shown, the pipe includes a valve arrangement 27 formed of stainless steel for regulating the fuel flow as the fuel falls from the header tank in a direction towards the collection tank. The tanks are conveniently formed of stainless steel. Each tank has a removable lid and vent hole. The various rig components have typically the dimensions as specified in the Figure.

Advantageously, the test rig is arranged such as to adopt two different drop heights and incorporates different interchangeable UV sterilisation units, as and when required.

A series of water trials were conducted in the test rig to identify leaks, and to ensure the correct flow rates and the UV device were operating in accordance with the refuel conditions of an aircraft. The rig was also routinely swabbed and sterilised to ensure that natural microbial contamination did not occur. Once it was established that the tests could be conducted safely and repeatedly with water, the rig was disinfected, rinsed, drained and thoroughly dried prior to commencing fuel tests.

A2. Flow Rates

The test rig was designed to work at a range of flow rates, providing a wide range of refuel conditions. From an irradiation point of view, the inventors found that it is the velocity of flow that was important and hence the exposure time. The calculated velocity range of a test aircraft refuelling was between:

Average refuel rate: 682 L/min=3.589 m/sec
Maximum certified refuel rate: 1250 L/min=6.578 m/sec Table 2 provides a summary of dimensions of a test aircraft fuel line and the flow rates, specifically as applied to all of the above described embodiments but for the ninth embodiment using the "elbow joint" section.

TABLE 2

Dimensions of a test aircraft fuel line and flow rates.

| | Fuel Pipe Diameter (") | Pipe Area (m$^2$) | Refuel Rate (L/min) | Refuel Pressure (psig) | Volumetric Flow Rate (m$^3$/s) | Fuel Velocity (m/s) |
|---|---|---|---|---|---|---|
| Test Aircraft | 2.5 (63.5 mm) | 3.167 × 10$^{-3}$ | 682 | 50 | 11.3667 × 10$^{-3}$ | 3.589 |
| Test Aircraft | 2.5 (63.5 mm) | 3.167 × 10$^{-3}$ | 1250 | 50 | 20.8333 × 10$^{-3}$ | 6.578 |

Flow velocity in the fuel pipe (2.5" diameter) was determined as follows:

The refuel rate (682 L/min) was converted to a volumetric flow rate (m3/s):

$$\dot{V} = \frac{682}{60 \times 1000} = 11.3667 \times 10^{-3} \text{ m}^3/\text{s}$$

The fuel velocity (v) was then calculated from the volumetric flow rate and the pipe cross-sectional area (A):

$$v = \frac{\dot{V}}{A} = \frac{11.3667 \times 10^{-3}}{3.167 \times 10^{-3}} = 3.589 \text{ m/s}$$

The head of fuel needed to achieve the required flow rate was determined (using the Bernoulli equation):

$$\frac{1}{2}\rho v^2 = \rho g h$$

$$h = \frac{v^2}{2g}$$

Where ρ=density of fluid, g=acceleration due to gravity, h=head (height of fluid)

$$h = \frac{v^2}{2g} = \frac{(3.589)^2}{2 \times 9.81} = 0.66 \text{ m}$$

Table 3 gives an indication of the head height required to achieve 682 L/min. This is based upon the above calculation and does not include the effects of frictional loss within the pipe or losses associated with pipe entry, exit and within the valves and connectors. Generally entry losses are negligible in such systems; so it is only necessary to make allowances for friction, exit and valve losses.

TABLE 3

Head height required to achieve maximum flow for the above pipe diameter.

| | Pipe Ø (mm) | Pipe Area (m$^2$) | Flow Rate (m$^3$/s) | Velocity (m/s) | Head (m) | Volumetric flow rate of Fuel (L/sec) |
|---|---|---|---|---|---|---|
| Test Aircraft | 63.5 | 3.167 × 10$^{-3}$ | 11.3667 × 10$^{-3}$ | 3.589 | 0.657 | 11.366 (682 L/min) |

Friction losses were estimated using Darcy's equation, together with friction factors for stainless steel pipe and Jet A1 (Massey, 1979). On the assumption that the pipe system comprised a half meter long irradiation section, calculations were undertaken for the friction losses for this component at a range of flow velocities. The calculations were undertaken assuming a relative roughness factor appropriate to commercial stainless steel pipe (roughness factor K≈0.045 mm).

In order to keep the overall rig height manageable, a maximum test rig height of 5 m was thus set.

For a given length of pipe and flow velocity, friction losses (and the extra head of piping required to offset them) decrease sharply as pipe diameter increases. In order to remain within the rig height limitation it was therefore decided to use a 3" (76.2 mm) diameter feeder pipe to connect the reservoir (header tank) to the irradiation section. Friction loss calculations were undertaken for various lengths of 3" pipe and various flow velocities, as set out in Table 4. The calculations were undertaken assuming a relative roughness factor appropriate to commercial stainless steel pipe (roughness factor k≈0.045 mm).

TABLE 4

Frictional losses in various lengths of 3" (76.2 mm) pipe.

| PIPE | dia (m) | Kinematic Viscosity 0.0000035 Roughness factor k 0.000045 area (m$^2$) | length (m) | velocity (m/s) | k/dia | Jet A1 Steel pipe Re | f | Hf (m) |
|---|---|---|---|---|---|---|---|---|
| 3.0" | 0.0762 | 0.00456 | 0.30 | 2.431 | 0.000591 | 5.293E+04 | 0.0055 | 0.026 |
| 76.2 mm | 0.0762 | 0.00456 | 0.50 | 3.132 | 0.000591 | 6.819E+04 | 0.0054 | 0.071 |
| | 0.0762 | 0.00456 | 0.66 | 3.589 | 0.000591 | 7.814E+04 | 0.0053 | 0.120 |
| | 0.0762 | 0.00456 | 1.00 | 4.429 | 0.000591 | 9.644E+04 | 0.0051 | 0.268 |
| | 0.0762 | 0.00456 | 1.50 | 5.425 | 0.000591 | 1.181E+05 | 0.0050 | 0.585 |
| | 0.0762 | 0.00456 | 2.00 | 6.264 | 0.000591 | 1.364E+05 | 0.0050 | 1.039 |
| | 0.0762 | 0.00456 | 2.50 | 7.004 | 0.000591 | 1.525E+05 | 0.0049 | 1.608 |

In this way, the above tables can be used to determine a number of flow rates. For example, to simulate 682 L/min at the correct flow velocity of 3.589 m/s (as specified in Table 3) the rig height was determined as follows: Using Table 4, the height required to give that velocity in 3" piping was 0.66 m. To this figure we must include the frictional head loss (Hf), which is 0.12 m, plus losses within each of the sterilisation units.

No allowance was made for the losses associated with any valve that would be used to control the flow rate. It was difficult to assess what these losses might be. However, under the assumption that a "full bore" ball valve is to be employed, when such a valve is fully open the flow should be unrestricted. Hence, it seems reasonable to neglect any losses.

Exit losses (discharge losses) were estimated based on empirical evidence, which suggested that a value of 0.7 was reasonable. This resulted in a velocity discharge coefficient of approximately 0.9. Hence, the achieved velocities were slightly lower (about 10%) than expected from the above calculations.

Whilst we thus modelled the flow velocities appropriate to test aircraft in this way, we can further calculate higher flow velocities, more appropriate to larger aircraft. Higher flow velocities can be achieved by performing a similar calculation to that given above, and increasing the rig height accordingly. Therefore the rig was designed to accommodate various interchangeable lengths of 3" diameter down pipe, as shown in FIG. 1. The maximum allowable rig height was 5 m and the maximum head of 3" pipe that can be used was 3 m, thereby limiting the maximum flow rate that can be simulated to approximately 6 m/s (1714 L/min). Flow rates were also controlled by throttling the exit valve and timing the discharge of a known volume of fuel from the header tank.

Tank Sizing

Assuming that the drop height was between 1 m and 3 m, a large fuel suitable container was used as the header tank. The depth of fuel should not exceed 1% (30 mm) of the total drop distance; this provided a more continuous discharge rate. Given the quantities of fuel we wished to use (~80 liters), a tank of approximately 1 m$^2$ was required (see FIG. 1). A similar sized tank was also required to collect the fuel after testing.

In order to calibrate the test rig, it should further be noted that a float switch was fitted to the top tank and used to measure the time taken for 30 liters of 80 L of fuel to fall.

Controlled Fuel Contamination

A 205 liter barrel of JET A1 fuel was supplied by Air BP of Sunbury Business Park, Chertsey Road, Sunbury-upon-Thames, Middlesex, TW16 7 LN, UK (see link: www.bp-.com). The chemical composition of the JET A1 samples with its associated additives corresponded to that of designated JET A1 specification, ASTM D1655 (as specified in Table A). Upon arrival, three samples were taken from the barrel and incubated, confirming the fuel was sterile. This was continued routinely throughout the investigation in order to eliminate any cross-contamination or invalid results.

Fuel within the test rig was contaminated with a culture of *Bacillus subtilis*. This is a hardy bacteria, with a higher UV resistance than most (dosage required to inactivate is about 11,000 µW·sec/cm$^2$). *Bacillus subtilis* is also a good test micro-organism as Bacilli are known to corrode aircraft fuel tanks, specifically aluminium alloy 2024. This is important as hundreds of different species of organism are known to contaminate fuel, but only a select few have actually been shown to induce fuel tank corrosion (see Table B for example which lists optical powers (UV dose) required to inactivate 99.9% of various microorganisms (not fuel specific)). For a long time, corrosion was believed to be caused by *Hormoconis resinae* (also termed *Cladosporium resinae*), however recent research suggests that bacteria of the *Bacillus* species plus the two fungi, Aureobasidium and Penicillium are responsible (refer to McNamara, C.; Perry, T.; Leard, R.; Bearce, K.; Dante, J.; Mitchell, R. (2005). Corrosion of aluminium alloy 2024 by microorganisms isolated from aircraft fuel tanks. Biofouling 21 (5-6), pp. 257-265(9). Taylor and Francis Ltd). *Bacillus* is a good candidate for evaluation as it can be easily grown, handled and disposed of within the laboratories at the Advanced Technology Centre.

Prior to contamination of the fuel, colonies of *B. subtilis* were grown on nutrient agar plates at the Advanced Technology Centre. A single isolated colony was then extracted and diluted in large (1 liter) culture flasks. The culture flasks contained 250 ml of distilled water and one spatula full of nutrient broth granules (food). The flasks were then incubated at 37° C. for 2, 3, 4, 5 and 6 hours to give 5 different bacteria concentrations, labelled A-E (the shorter the incubation period, the fewer bacteria).

Bacteria were added to the sterile fuel as it was being pumped into the top header tank. A single culture flask was gradually poured into the 80 liters of JET A1 and the two liquids were thoroughly mixed. Three samples of the contaminated fuel were then taken from the header tank and incubated, to give an indication of the level of bacterial contamination in the fuel prior to UV exposure.

Sampling and Incubation

In order to assess the level of microbial growth very stringent sampling and incubation steps were followed.

All samples were taken with 0.5 ml sterile inoculation loops. These were immediately streaked (spread) onto sterile nutrient agar plates, sealed with Parafilm tape and then incubated for ~6 hours at 37° C. Normally any growth can be clearly seen by eye within this time period. If no visible growth appeared after 6 hours, the incubation period was extended to 24 hrs at 37° C. This additional incubation period was used to ensure that even very low levels of contamination would grow and be detected.

In order to reduce the risk of misleading results, three repeat samples plus control plates were normally incubated.

Irradiation of Contaminated Fuel

The UV bulbs were turned on and allowed to warm up for 10 minutes prior to experimentation. The manufacturer recommends a minimum warm-up period of 60-90 seconds; however, a longer time was permitted due to experimental set up constraints (contamination of the top tank and sampling procedure).

Once the bulbs were warm, the valve on the test rig was opened either fully or halfway, simulating the different velocities which may be encountered during aircraft refuelling. Three samples were taken ~1.5 seconds after opening the valve, i.e. when the flow had reached its maximum velocity.

In all instances fuel flowed freely through the UV chamber and no significant bubbling or opacity could be seen through the eye-safe window fitted to the side of the UV device.

Results—Sterilisation Efficiency

FIG. 2A to 2E show results from the test rig. As shown in the Figures, the level of contamination increased from A)-E) and this can be seen by the number of colony forming units (CFU) present (left hand plate of each image). The remaining two plates were irradiated samples that had been passed through the UV chamber. The middle plates all showed samples taken with the valve half open (780 L/min) and the plates on the right with the valve fully open (1210 L/min). In each instance the two plates with irradiated samples showed no growth after a full 24 hours of incubation. As previously mentioned three sample plates were taken for each bacteria concentration, the results presented being representative of those seen on the other sample plates. In early fuel trials, single colonies (i.e. one single white spot, which would indicate one single bacterium) were found on two separate ½ open valve tests. This result was not repeated in the two back-up plates taken at the same time. As this happened twice at two separate instances, it suggested that an extremely low concentration of bacteria may get through (~1 in several million typically). These results illustrated that UV light can be used to sterilise JET A1 contaminated with both high and low levels of bacteria. In addition, the results strongly suggest that the UV kill rate is close to approaching 100% efficiency at both velocities.

Referring again to FIG. 2, in each image the plate on the left is the sample taken from the header tank and indicates the level of bacteria in the fuel. The middle plate is the sample taken after UV treatment with the valve ½ open (780 L/min). The plate on the right is the sample taken after UV treatment with the valve fully open (1210 L/min). Some condensation can be seen on the underside of all the plates, and this is due to the fact that the plates were stored in the refrigerator prior to photographing.

Temperature

Thermocouple sensors were placed in the fuel rig in order to monitor the temperature of the bulbs and the fuel. Prior to the fuel trials, it had been determined that the UV bulbs would not exceed the auto-ignition point (210° C.) of JET A1 fuel. However, further safety trials were conducted under simulated refuel conditions to confirm that this was so.

Free Flowing Fuel Test

This experiment was carried out to determine the rise in fuel temperature during standard refuel conditions. The bulbs had been switched on for 1 hour prior to tests and the fuel rig valve was ½ open to allow continuous recirculation of the fuel. Table 5 below provides a summary of the temperature measurements as recorded during simulated refuel conditions.

TABLE 5

Temperature measurements recorded during simulated refuel conditions.

| | |
|---|---|
| Bulb Surface Temperature: | 65.2° C. |
| Room Temperature: | 12.3° C. |
| Fuel Temperature immediately before test: | 9.7° C. |
| Mean Fuel Temperature during recirculation at 780 L/min: | 10.6° C. |

Please note that this experiment was not conducted with the valve fully open because we did not have permission from the on-site fire authority to use the considerably larger quantity of fuel that would be required in order to recirculate continuously at 1025 L/min. However, at the higher flow rate the measured temperature would be similar to or even slightly lower than that recorded above, bearing in mind that the faster-moving fuel would be exposed to the heat source for a shorter period of time.

Fuel Blockage Tests

The test rig was used to simulate a number of worse case scenarios. In this experiment the temperatures of the bulbs and fuel were recorded whilst there was a simulated blockage. The rig was filled with fuel and the bulbs left on with the valve closed (FIG. 3). The results showed that the surface of the bulbs reached a maximum temperature of 65.2° C. and that the blocked fuel within the chamber rose by only 2.9° C. (above ambient starting temperature of 11.0° C.) over the course of 1 hour.

Fuel Vapour Tests

This experiment was carried out to simulate the effect of leaving the bulbs on whilst the UV chamber was blocked and full of fuel vapour (FIG. 4). The results showed that the surface of the bulbs reached a maximum temperature of 59.9° C. and that the vapour temperature rose by 13.6° C., to 24.6° C.

In all instances the temperature trials indicated that UV bulbs do not present a significant or dangerous heat source, providing they are maintained in a spark free environment.

Extreme Temperatures

During flight the outside temperature drops significantly. In addition, during ascent and descent the temperature may change. If a UV unit were to be fitted to an aircraft, the bulbs must not be damaged by these temperature extremes. Issues could include the condensation of the gasses within the fluorescent bulbs, or damage to the filaments as they chill and possibly crack.

Fuel tanks can get as cold as −30° C. during flight—this is above the −47° C. freezing point of Jet A1. However, in colder climates such as northern Canada, flight temperatures can exceed this and as a consequence Jet B is used, which has a freezing point of −51° C. Fuel's temperature during refuel is typically between 0° C. and 10° C. and it is envisaged that an aircraft would not be refuelled at temperatures below −20° C. However, these would routinely be chilled and required to operate afterwards. In order to test their performance, UVC bulbs were placed in an environmental chamber and chilled. The bulbs were switched on, observed and then off at every 5° C. interval to a maximum of −60° C.

The chamber trials showed that the bulbs will still operate at −60° C. The bulbs did not appear to be damaged and when taken from −60° C. to +12° C. (in 8 minutes), the bulb operated as normal.

In this connection, the inventors have proposed that cyclic temperature trials are conducted on any proposed UV unit that is to be aircraft mounted.

It is to be understood that any feature described in relation to any one embodiment or Example may be used alone, or in combination with other features described, and may also be used in combination with one or more features of any other of the embodiments or Examples, or any combination of any other of the embodiments and Examples.

Furthermore, equivalents and modifications not described above may also be employed without departing from the scope of the invention, which is defined in the accompanying claims. For example, the performance of the above described embodiments at other different UV wavelengths could potentially be improved, if desired, by provision of other different UV light sources including LEDs, optical fibres and X elements (see Appendix A hereinafter) in place of mercury bulbs. Modification of the shapes/sizes of the above described arrangements could be made to accommodate this possibility. The UV irradiation intensity could also be increased or decreased, as desired, by provision of additional sources at different predetermined locations (with or without additional UV transparent windows) or by reducing the number of sources. Further, whilst in the described embodiments the same designated JET A1 specification was treated by UV irradiation, it is to be appreciated that other compositions of JET A1 as well as compositions of other jet/aviation fuels, and indeed compositions of other different fuels could be effectively treated by UV irradiation by appropriate selection of the fuel/fuel flow rate, the UV dose (refer to Table B) and other standard parameters. Further, because the above-discussed UV sterilisation unit of the invention is modular, several such units could be installed on aircraft for example, in parallel or series in order to improve the sterilisation efficiency.

It is to be further appreciated that the above described UV irradiation unit in accordance with the above described embodiments of the invention could be mounted at a predetermined location inside a fuel storage vessel or in the tank of a bowser. As applied to aircraft for example, UV bulbs mounted in a portable inspection light type of housing could be placed in the access panels on the underside of the wing(s). One advantage of such an arrangement is that it enables direct treatment of the fuel tanks by means of controlled exposure of the tanks to UV light (thereby protecting the inside of the tanks).

It is also to be appreciated that the invention has utility for many different fuel system applications, for example in aircraft, ships, submarines and in other motive vehicles. It may also be desirable to apply the UV sterilisation unit of the invention to petrol station forecourts. As described above, the UV sterilisation unit of the invention can also be mounted, if desired, on different fuel platforms including bowsers.

APPENDIX A

Viable UV Light Sources for Use in the Invention

The following consideration was given to viable UV light sources for use in the invention.

Bulbs and Lamps
Mercury Bulbs

As described above. Note that these sources can be coupled to a light guide/rod and this can be used as a solution for directing light within surge tanks (see ninth embodiment described above).

X Elements

Osram are known to make a series of fluorescent lamps that are specifically for use in explosive environments. At present, these are used for conventional lighting, normally on gas and oil rigs. However, it is recognised that the same element could possibly be used in a UVC bulb, specific for our inventive applications.

Type X fluorescent tubes are characterised by having a single contact pin at each end of the tube. The design of the lamp is similar to T12 fluorescent tubes, but the single pin connection prevents the X type lamps from being used in normal 'cathode preheat' circuits. The fact that the cathodes have no means of being electrically heated means that they pose no risk of being a source of ignition in an explosive atmosphere.

Mercury Arc Lamps

These lamps have the same optical properties as mercury bulbs, but the light is delivered in a less dispersed manner. This means that lenses can be used to focus the light on to a fibre optic bundle. Cost of the bulbs is currently approximately £50. The disadvantages are that the bulbs need to warm up before use (20-30 minutes) and their operational lifetime is significantly shorter at 100-400 hours.

Xenon Arc Lamps

These lamps can also be used as a UV source as they have a broad optical output. This ranges from 200-1000 nm, with peaks at 250, 840 and 900 nm. These have the same issues as mercury arc lamps (see above), and also emit infrared (so require further cooling).

Deuterium Arc Lamps

These lamps emit a broad optical output (190-400 nm), with predominant UV light and no IR. These again require a significant warm up period and have a limited lifetime.

Arc lamp housings, which include collimating optics suitable for coupling light to fibre optic bundles, are available.

LEDs

Light Emitting Diodes (LEDs) are considered potentially to be a practical alternative to the mercury bulbs we have used in the embodiments. These sources provide the potential for considerably lower heat output, smaller size and increased optical efficiency. However, at present, short wavelength UV LEDs are not commercially available. Research level (developmental) LEDs are currently available, but at considerable cost and with no guaranteed operational lifetime.

Optical Fibres

Specialist fibre optics (see for example the link: www.avantes.com) are required for UV transmission (this is because standard glass and plastics absorb UV at the range we are interested in). As a result, the fibres are slightly more expensive, but attenuation losses are negligible. Currently, the cost of the fibre is typically about £133 per meter.

The invention claimed is:

1. A method of treating a flammable material, comprising: providing a flammable material that includes a biofuel; and irradiating the flammable material with predominantly ultra-violet radiation for causing a proportion of microorganisms in the flammable material to be sterilized.

2. The method of claim 1, wherein the biofuel is a liquid fuel.

3. The method of claim 1, wherein irradiating the flammable material with predominantly ultra-violet radiation includes irradiating the flammable material with ultra-violet radiation in a wavelength range of between about 100 nm and 290 nm.

4. The method of claim 1, wherein irradiating the flammable material includes irradiating the flammable material with ultra-violet radiation in a wavelength range of between about 240 nm and 280 nm.

5. The method of claim 4, wherein said ultra-violet radiation has a wavelength predominantly at 254 nm.

6. The method of claim 1, wherein irradiating the flammable material includes irradiating the flammable material with at least 2500 micro-Watt seconds per square centimeter of ultra-violet radiation.

7. The method of claim 1, wherein the proportion of microorganisms is greater than 99%.

8. A method of treating a flammable material, comprising:
provided a flammable material that includes JET A1 liquid aviation jet fuel; and
irradiating the flammable material with predominantly ultra-violet radiation for causing a proportion of microorganisms in the flammable material to be sterilized.

9. The method of claim 8, wherein irradiating the flammable material includes irradiating the flammable material with ultra-violet radiation in a wavelength range of between about 100 nm and 290 nm.

10. The method of claim 8, wherein irradiating the flammable material includes irradiating the flammable material with ultra-violet radiation in a wavelength range of between about 240 nm and 280 nm.

11. The method of claim 10, wherein said ultra-violet radiation has a wavelength predominantly at 254 nm.

12. A method of treating a flammable material, comprising:
providing a flammable material that includes fuel vapor; and
irradiating the flammable material by treating the fuel vapor in a fluid with predominantly ultra-violet radiation for causing a proportion of microorganisms in the flammable material to be sterilized.

13. The method of claim 8, wherein irradiating the flammable material includes irradiating the flammable material with at least 2500 micro-Watt seconds per square centimeter of ultra-violet radiation.

14. The method of claim 8, wherein the proportion of microorganisms is greater than 99%.

15. The method of claim 12, wherein irradiating the flammable material includes irradiating the flammable material with ultra-violet radiation in a wavelength range of between about 100 nm and 290 nm.

16. The method of claim 12, wherein irradiating the flammable material includes irradiating the flammable material with ultra-violet radiation in a wavelength range of between about 240 nm and 280 nm.

17. The method of claim 16, wherein said ultra-violet radiation has a wavelength predominantly at 254 nm.

18. The method of claim 12, wherein irradiating the flammable material includes irradiating the flammable material with at least 2500 micro-Watt seconds per square centimeter of ultra-violet radiation.

19. The method of claim 12, wherein the proportion of microorganisms is greater than 99%.

* * * * *